US008119819B2

(12) United States Patent
Arrhenius et al.

(10) Patent No.: US 8,119,819 B2
(45) Date of Patent: Feb. 21, 2012

(54) MALONYL-COA DECARBOXYLASE INHIBITORS USEFUL AS METABOLIC MODULATORS

(75) Inventors: Thomas Arrhenius, Del Mar, CA (US); Mi Chen, San Diego, CA (US); Jie Fei Cheng, Carlsbad, CA (US); Yujin Huang, San Diego, CA (US); Alex Michael Nadzan, Encinitas, CA (US); Richard Julius Penuliar, San Diego, CA (US); David Mark Wallace, San Diego, CA (US); Lin Zhang, San Diego, CA (US); Gary D. Lopaschuk, Edmonton (CA); Jason R. Dyck, Sherwood Park (CA)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 235 days.

(21) Appl. No.: 12/431,720

(22) Filed: Apr. 28, 2009

(65) Prior Publication Data

US 2010/0016259 A1 Jan. 21, 2010

Related U.S. Application Data

(62) Division of application No. 10/466,923, filed as application No. PCT/US02/01789 on Jan. 22, 2002, now Pat. No. 7,524,969.

(60) Provisional application No. 60/264,552, filed on Jan. 26, 2001.

(51) Int. Cl.
*C07D 207/30* (2006.01)
(52) U.S. Cl. .................... 548/560; 548/565
(58) Field of Classification Search ............. 548/560, 548/565
See application file for complete search history.

(56) References Cited

U.S. PATENT DOCUMENTS

| 3,666,769 | A | 5/1972 | Jones et al. |
|---|---|---|---|
| 4,381,311 | A | 4/1983 | Haber |
| 4,632,930 | A | 12/1986 | Carini et al. |
| 5,177,097 | A | 1/1993 | Poss |
| 5,190,942 | A | 3/1993 | Poss |
| 5,208,234 | A | 5/1993 | Poss |
| 5,208,235 | A | 5/1993 | Poss |
| 5,212,177 | A | 5/1993 | Poss |
| 5,225,408 | A | 7/1993 | Weller |
| 5,256,695 | A | 10/1993 | Poss |
| 5,374,615 | A | 12/1994 | Poss |
| 5,378,704 | A | 1/1995 | Weller |
| 5,428,033 | A | 6/1995 | Belley |
| 5,470,975 | A | 11/1995 | Atwal |
| 5,512,681 | A | 4/1996 | Boswell |
| 5,519,143 | A | 5/1996 | Harris |
| 5,534,347 | A | 7/1996 | Chen |
| 5,736,297 | A | 4/1998 | Roeschert |
| 5,895,771 | A | 4/1999 | Epstein |
| 5,977,413 | A | 11/1999 | Tomaru |
| 6,492,353 | B1 | 12/2002 | Manchand et al. |

FOREIGN PATENT DOCUMENTS

| DE | 197 16 231 A1 | 10/1998 |
|---|---|---|
| DE | 197 22 952 A1 | 12/1998 |
| EP | 0 481 448 A1 | 4/1992 |
| EP | 0 547 442 A1 | 6/1993 |
| EP | 0 556 060 A1 | 8/1993 |
| EP | 0 733 366 A2 | 9/1996 |
| EP | 0 733 614 A1 | 5/1998 |
| EP | 0 296 722 A1 | 12/1998 |
| EP | 0 916 352 A2 | 12/1998 |
| FR | 2 784 114 A1 | 4/2000 |
| GB | 2 321 244 A | 7/1998 |
| GB | 2 337 701 A | 1/1999 |
| JP | 57-134480 | 8/1982 |
| JP | 08-311036 | 11/1996 |
| JP | 09-012585 | 1/1997 |
| JP | 95-12795 | 12/1997 |
| JP | 2007-185377 | 7/2007 |
| RU | 1825496 A3 | 12/1994 |
| RU | 1743153 | 2/1995 |
| WO | WO 87/05297 | 9/1987 |
| WO | WO 91/00277 | 1/1991 |
| WO | WO 91/00281 | 1/1991 |
| WO | WO 92/00067 | 1/1992 |
| WO | WO 93/21158 | 10/1993 |

(Continued)

OTHER PUBLICATIONS

Cheng et al. Journal of Medicinal Chemistry (2006), 49(14), 4055-4058.*
Database Registry Chemical Abstracts Service, Columbus, Ohio, US, Dec. 6, 2000, retrieved from STN.
Gavrilova et al., "Fluorine Derivatives of the Furan Series—I—Synthesis of Fluorine-Containing Alcohols of the Furan Series", Zhurnal Organicheskoi Khimii, vol. 26, No. 11, pp. 2087-2089, Nov. 1990, original article submitted Oct. 27, 1987.

(Continued)

*Primary Examiner* — Nizal Chandrakumar
*Assistant Examiner* — Nizal S Chandrakumar
(74) *Attorney, Agent, or Firm* — Fish & Richardson P.C.

(57) ABSTRACT

The present invention relates to novel compounds (I), their prodrugs, and the pharmaceutically acceptable salts as well as pharmaceutical compositions containing such compounds useful in treating certain metabolic diseases and diseases modulated by the inhibition of the enzyme malonyl-coenzyme A decarboxylase (malonyl-CoA decarboxylase, MCD). In particular, the invention relates to compounds and compositions and the methods for the prophylaxis, management and treatment of cardiovascular diseases, diabetes, acidosis, cancers, and obesity through the inhibition of malonyl-coenzyme A decarboxylase.

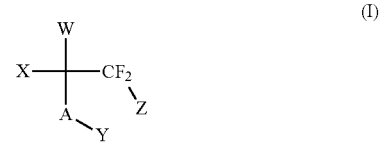

(I)

4 Claims, No Drawings

FOREIGN PATENT DOCUMENTS

| WO | WO 93/21168 | 10/1993 |
| --- | --- | --- |
| WO | WO 94/10692 | 5/1994 |
| WO | WO 94/14453 | 7/1994 |
| WO | WO 94/15932 | 7/1994 |
| WO | WO 94/18606 | 8/1994 |
| WO | WO 95/35311 | 12/1995 |
| WO | WO 95/35312 | 12/1995 |
| WO | WO 95/35313 | 12/1995 |
| WO | WO 96/13491 | 5/1996 |
| WO | WO 96/13500 | 5/1996 |
| WO | WO 99/12938 | 3/1999 |
| WO | WO 99/47497 | 9/1999 |
| WO | WO 99/65884 | 12/1999 |
| WO | WO 00/20472 | 4/2000 |
| WO | WO 00/34344 | 6/2000 |
| WO | WO 00/37422 | 6/2000 |
| WO | WO 00/46203 | 8/2000 |
| WO | WO 00/54759 | 9/2000 |
| WO | WO 00/56710 | 9/2000 |
| WO | WO 01/03705 A1 | 1/2001 |
| WO | WO 02/058690 A2 | 8/2002 |
| WO | WO 02/064136 | 8/2002 |

OTHER PUBLICATIONS

Gavrilova et al., "Fluorine Derivatives of the Furan Series—II—Reaction of the Hydroxy Group in Fluorine-Containing Furan Alcohols", Zhurnal Organicheskoi Khimii, vol. 26, No. 11, pp. 2090-2094, Nov. 1990, original article submitted Oct. 27, 1987.

Ohira et al., "Preparation of (22S)- and (22R)-24-homo-26,26,26,27,27,27-hexafluoro -1,22,25-trihydroxy1-24-yne-vitamin D3", Chemical & Pharmaceutical Bulletin, vol. 40, No. 6, Jun. 1992, pp. 1647-1649.

Zelenin et al., "Reactions of Indoles with Polyfluorocarbonyl Compounds", Chemistry of Heterocyclic Compounds, vol. 23, No. 9, Sep. 1987, pp. 959-961.

Database Crossfire; Beilstein Institut zur Foerderung der Chemischen Wisenschaften, Beilstein Registry No. 4505552, 1975.

Database Crossfire; Beilstein Institut zur Foerderung der Chemischen Wisenschaften, Beilstein Registry No. 4756314, 1990.

Gilbert, E., "Perhaloketones XIX(1)", Journal of Heterocyclic Chemistry, vol. 6, Aug. 1969, pp. 483-490.

Righetti et al., "Heterodiene synthesis—XXIV" Tetrahedron, vol. 37, No. 9, 1981, pp. 1779-1785.

Bravo et al., "An Efficient Entry to Perfluoroallcyl Azoles Starting from Beta-Perfluoroalkyl-Beta-Dicarbonyl Compounds", Tetrahedron, vol. 50, No. 29, 1994, pp. 8827-8836.

Birkinshaw et al., "?2-N,N-Disubstituted Amino) Thiazoles with Electro-withdrawing Groups at Position 5: Preparation and Investigation of Structural Features, Journal of the Chemical Society, Perkins Transactions 1, No. 2, 1984, pp. 147-153.

Clerin et al., "Hétérocyclisation des alpha-acylamioamides, II.—l'hétérocyclisation des amides alpha-aclaminés tertiaires", Bulletin de la Societe Chimique de France, No. 11, 1973, pp. 3134-3142.

Franot et al., "Chemical Models Studies on the Monoamine Oxidase-B Catalyzed Oxidation of 4-substitued 1-methyl-1, 2, 3, 6-tetrahydropyridines", Biorganic and Medicinal Chemistry, vol. 5, No. 8, 1997, pp. 1519-1529.

Fujii et al., "Thermal Condensation of Substituted Imidazoles with Trifluoroacetaldehyde", Journal of Fluorine Chemistry, vol. 32, No. 3., 1986, pp. 329-343.

Kawase, M., "A Novel Ring Transformation of Mesoionic 1,3-oxazolium-5-olates into 5-trifluoroacetylated and 5-perfluoroacylated imidazoles by Reaction with Amidines", Journal of the Chemical Society, Chemical Communications, No. 18, 1994, pp. 2101-2102.

King, R., "Derivatization of Ethylenethiourea with m-trifluoromethylbenzyl chloride for Analysis by Electron-capture Gas Chromatography", Journal of Agricultural and Food Chemistry, vol. 25, No. 1, 1997, pp. 73-75.

Sewald et al., "Synthese 2-Heteroaryl-substituierter 3,3,3-trifluoroalanin-und 3,3,3-Trifluoromilchsäure-Derivate", Liebigs Annalen der Chemie, No. 9, 1992, pp. 947-952.

Abo-Hashema, et al., Biochemistry, 1999, 15840-15847, vol. 38.

Abo-Hashema, et al., Journal of Biological Chemistry, 1999, 35577-35582, Vo. 274, No. 50.

Alam and Sagggerson, Biochen J., 1998, 233-241, vol. 334.

An, et al., Journal of Biochemistry and Molecular Biology, 1999, 414-418, vol. 32, No. 4.

Anderson, Current Pharmaceutical Design, 1998, 1-16, vol. 4, No. 1.

Buckner, et al., Archives of Biochemistry and Biophysics, 1976, 539-551, vol. 177.

Deems, et al., The American Physiological Society, 1998, R524-R528, vol. 274.

Dyck, et al., The American Physiological Society, 1998, H2122-H2129, vol. 275.

Fitzpatrick, et al., Am. J. Hum. Genet. 1999, 318-326, vol. 65.

Fraser, et al., Febs Letters, 1999, 69-74, vol. 446.

Gao, et al., Journal of Lipid Research, 1999, 178-182, vol. 40.

Hearse, Metabolic Approaches to Ischaemic Heart Disease and its Management, Science Press, London, UK.

Jang, et al., The Journal of Biological Chemistry, 1989, 3500-3505, vol. 264, No. 6.

Kantor, et al., Circulation Research, 2000, 580-588, vol. 86.

Kennedy, et al., Biochemical Pharmacology, 1996, 273-280, vol. 52.

Kim and Kolattukudy, Archives of Biochemistry and Biophysics, 1978, 585-597, vol. 190, No. 2.

Kim and Kolattukudy, Archives of Biochemistry and Biophysics, 1978, 234-246, vol. 190, No. 1.

Kim and Kolattukudy, Biochemica et Biophysica Acta, 1978, 187-196, vol. 531.

Loftus, et al., Science, 2000, 273-238, vol. 288.

McCormack, et al., Gen. Pharmac., 1998, 639-645, vol. 30, No. 5.

McGarry and Brown, Eur. J. Biochem, 1997, 1-14, vol. 244.

McNeill, Measurement of Cardiovascular Func., CRC Press, Boca Raton, USA.

Pepine and Wolff, The American Journal of Cardiology, 1999, 46-50, vol. 84.

Pizer, et al., Cancer Research, 2000, 213-218, vol. 60.

Prentki and Corkey, Diabetes, 1996, 273-283, vol. 45.

Randle, et al., Lancet, 1963, 785-789, vol. 1.

Sacksteder, et al., The Journal of Biological Chemistry, 1999, 24461-24468, vol. 274, No. 35.

Voilley, et al., Biochem J., 1999, 213-217, vol. 340.

Wargovich, et al., Am J Cardiol, 1988, 65-70, vol. 61.

Zammit, Biochemical Society, 1999, 505-515, vol. 343.

* cited by examiner

MALONYL-COA DECARBOXYLASE INHIBITORS USEFUL AS METABOLIC MODULATORS

This application is a divisional of application Ser. No. 10/466,923 filed Jul. 21, 2003, now U.S. Pat. No. 7,524,969, which is a U.S. national phase application under 35 U.S.C. §371(c) of international application no. PCT/US2002/001789, filed Jan. 22, 2002 which claims the benefit of provisional application Ser. No. 60/264,552 filed on Jan. 26, 2001, the entire disclosure of which is incorporated herein by reference.

FIELD OF THE INVENTION

The present invention relates to novel compounds, their prodrugs, and the pharmaceutically acceptable salts as well as pharmaceutical compositions containing such compounds useful in treating certain metabolic diseases and diseases modulated by the inhibition of the enzyme malonyl-coenzyme A decarboxylase (malonyl-CoA decarboxylase, MCD). In particular, the invention relates to compounds and compositions and the methods for the prophylaxis, management and treatment of cardiovascular diseases, diabetes, acidosis, cancers, and obesity through the inhibition of malonyl-coenzyme A decarboxylase.

BACKGROUND

Malonyl-CoA is an important metabolic intermediary produced by the enzyme Acetyl CoA Carboxylase (ACC) in the body. In the liver, adipocytes, and other tissues, malonyl-CoA is a substrate for fatty acid synthase (FAS). ACC and malonyl-CoA are found in skeletal muscle and cardiac muscle tissue, where fatty acid synthase levels are low. The enzyme malonyl-CoA decarboxylase (MCD, EC 4.1.1.9) catalyzes the conversion of malonyl-CoA to acetyl-CoA and thereby regulates malonyl-CoA levels. MCD activity has been described in a wide array of organisms, including prokaryotes, birds, and mammals. It has been purified from the bacteria *Rhizobium trifolii* (An et al., *J. Biochem. Mol. Biol.* 32:414-418 (1999)), the uropygial glands of waterfowl (Buckner, et al., *Arch. Biochem. Biophys* 177:539 (1976); Kim and Kolattukudy *Arch. Biochem. Biophys* 190:585 (1978)), rat liver mitochondria (Kim and Kolattukudy, *Arch. Biochem. Biophys.* 190:234 (1978)), rat mammary glands (Kim and Kolattukudy, *Biochim. Biophys, Acta* 531:187 (1978)), rat pancreatic β-cell (Voilley et al., *Biochem. J.* 340:213 (1999)) and goose (*Anser anser*) (Jang et al., *J. Biol. Chem.* 264:3500 (1989)). Identification of patients with MCD deficiency lead to the cloning of a human gene homologous to goose and rat MCD genes (Gao et al., *J. Lipid. Res.* 40:178 (1999); Sacksteder et al., *J. Biol. Chem.* 274:24461 (1999); FitzPatrick et al., *Am. J. Hum. Genet.* 65:318 (1999)). A single human MCD mRNA is observed by Northern Blot analysis. The highest mRNA expression levels are found in muscle and heart tissues, followed by liver, kidney and pancreas, with detectable amounts in all other tissues examined.

Malonyl-CoA is a potent endogenous inhibitor of carnitine palmitoyltransferase-I (CPT-I), an enzyme essential for the metabolism of long-chain fatty acids. CPT-I is the rate-limiting enzyme in fatty acid oxidation and catalyzes the formation of acyl-carnitine, which is transported from the cytosol across the mitochondrial membranes by acyl carnitine translocase. Inside of the mitochondria the long-chain fatty acids are transferred back to CoA form by a complementary enzyme, CPT-II, and, in the mitochondria, acyl-CoA enters the β-oxidation pathway generating acetyl-CoA. In the liver, high levels of acetyl-CoA occurs for example following a meal, leading to elevated malonyl-CoA levels, which inhibit CPT-I, thereby preventing fat metabolism and favoring fat synthesis. Conversely, low malonyl-CoA levels favor fatty acid metabolism by allowing the transport of long-chain fatty acids into the mitochondria. Hence, malonyl-CoA is a central metabolite that plays a key role in balancing fatty acid synthesis and fatty acid oxidation (Zammit, *Biochem. J.* 343: 5050-515 (1999)). Recent work indicates that MCD is able to regulate cytoplasmic as well as mitochondrial malonyl-CoA levels [Alam and Saggerson, *Biochem J.* 334:233-241 (1998); Dyck et al., *Am J Physiology* 275:H2122-2129 (1998)].

Although malonyl-CoA is present in muscle and cardiac tissues, only low levels of FAS have been detected in these tissues. It is believed that the role of malonyl-CoA and MCD in these tissues is to regulate fatty acid metabolism. This is achieved via malonyl-CoA inhibition of muscle (M) and liver (L) isoforms of CPT-I, which are encoded by distinct genes (McGarry and Brown, *Eur. J. Biochem.* 244:1-14 (1997)). The muscle isoform is more sensitive to malonyl-CoA inhibition ($IC_{50}$ 0.03 µM) than the liver isoform ($IC_{50}$ 2.5 µM). Malonyl-CoA regulation of CPT-I has been described in the liver, heart, skeletal muscle and pancreatic β-cells. In addition, malonyl-CoA sensitive acyl-CoA transferase activity present in microsomes, perhaps part of a system that delivers acyl groups into the endoplasmic reticulum, has also been described (Fraser et al., *FEBS Lett.* 446: 69-74 (1999)).

Cardiovascular Diseases: The healthy human heart utilizes available metabolic substrates. When blood glucose levels are high, uptake and metabolism of glucose provide the major source of fuel for the heart. In the fasting state, lipids are provided by adipose tissues, and fatty acid uptake and metabolism in the heart down regulate glucose metabolism. The regulation of intermediary metabolism by serum levels of fatty acid and glucose comprises the glucose-fatty acid cycle (Randle et al., *Lancet*, 1:785-789 (1963)). Under ischemic conditions, limited oxygen supply reduces both fatty acid and glucose oxidation and reduces the amount of ATP produced by oxidative phosphorylation in the cardiac tissues. In the absence of sufficient oxygen, glycolysis increases in an attempt to maintain ATP levels and a buildup of lactate and a drop in intracellular pH results. Energy is spent maintaining ion homeostasis, and myocyte cell death occurs as a result of abnormally low ATP levels and disrupted cellular osmolarity. Additionally, AMPK, activated during ischemia, phosphorylates and thus inactivates ACC. Total cardiac malonyl-CoA levels drop, CPT-I activity therefore is increased and fatty acid oxidation is favored over glucose oxidation. The beneficial effects of metabolic modulators in cardiac tissue are the increased efficiency of ATP/mole oxygen for glucose as compared to fatty acids and more importantly the increased coupling of glycolysis to glucose oxidation resulting in the net reduction of the proton burden in the ischemic tissue.

A number of clinical and experimental studies indicate that shifting energy metabolism in the heart towards glucose oxidation is an effective approach to decreasing the symptoms associated with cardiovascular diseases, such as but not limited, to myocardial ischemia (Hearse, "*Metabolic approaches to ischemic heart disease and its management*", Science Press). Several clinically proven anti-angina drugs including perhexyline and amiodarone inhibit fatty acid oxidation via inhibition of CPT-I (Kennedy et al., *Biochem. Pharmacology*, 52: 273 (1996)). The antianginal drugs ranolazine, currently in Phase III clinical trials, and trimetazidine are shown to inhibit fatty acid β-oxidation (McCormack et al., *Genet. Pharmac.* 30:639 (1998), Pepine et al., *Am. J. Cardiology*

84:46 (1999)). Trimetazidine has been shown to specifically inhibit the long-chain 3-ketoactyl CoA thiolase, an essential step in fatty acid oxidation. (Kantor et al., *Circ. Res.* 86:580-588 (2000)). Dichloroacetate increases glucose oxidation by stimulating the pyruvate dehydrogenase complex and improves cardiac function in those patients with coronary artery diseases (Wargovich et al., *Am. J. Cardiol.* 61:65-70 (1996)). Inhibiting CPT-I activity through the increased malonyl-CoA levels with MCD inhibitors would result in not only a novel, but also a much safer method, as compared to other known small molecule CPT-I inhibitors, to the prophylaxis and treatment of cardiovascular diseases.

Most of the steps involved in glycerol-lipid synthesis occur on the cytosolic side of liver endoplasmic reticulum (ER) membrane. The synthesis of triacyl glycerol (TAG) targeted for secretion inside the ER from diacyl gycerol (DAG) and acyl CoA is dependent upon acyl CoA transport across the ER membrane. This transport is dependent upon a malonyl-CoA sensitive acyl-CoA transferase activity (Zammit, *Biochem. J.* 343: 505 (1999) Abo-Hashema, *Biochem.* 38: 15840 (1999) and Abo-Hashema, *J. Biol. Chem.* 274:35577 (1999)). Inhibition of TAG biosynthesis by a MCD inhibitor may improve the blood lipid profile and therefore reduce the risk factor for coronary artery disease of patients.

Diabetes: Two metabolic complications most commonly associated with diabetes are hepatic overproduction of ketone bodies (in NIDDM) and organ toxicity associated with sustained elevated levels of glucose. Inhibition of fatty acid oxidation can regulate blood-glucose levels and ameliorate some symptoms of type II diabetes. Malonyl-CoA inhibition of CPT-I is the most important regulatory mechanism that controls the rate of fatty acid oxidation during the onset of the hypoinsulinemic-hyperglucagonemic state. Several irreversible and reversible CPT-I inhibitors have been evaluated for their ability to control blood glucose levels and they are all invariably hypoglycemic (Anderson, *Current Pharmaceutical Design* 4:1 (1998)). A liver specific and reversible CPT-inhibitor, SDZ-CPI-975, significantly lowers glucose levels in normal 18-hour-fasted nonhuman primates and rats without inducing cardiac hypertrophy (Deems et al., *Am. J. Physiology* 274:R524 (1998)). Malonyl-CoA plays a significant role as a sensor of the relative availability of glucose and fatty acid in pancreatic β-cells, and thus links glucose metabolism to cellular energy status and insulin secretion. It has been shown that insulin secretagogues elevate malonyl-CoA concentration in β-cells (Prentki et al., *Diabetes* 45: 273 (1996)). Treating diabetes directly with CPT-I inhibitors has, however, resulted in mechanism-based hepatic and myocardial toxicities. MCD inhibitors that inhibit CPT-I through the increase of its endogenous inhibitor, malonyl-CoA, are thus safer and superior as compared to CPT-I inhibitors for treatment of diabetic diseases.

Cancers: Malonyl-CoA has been suggested to be a potential mediator of cytotoxicity induced by fatty-acid synthase inhibition in human breast cancer cells and xenografts (Pizer et al., *Cancer Res.* 60:213 (2000)). It is found that inhibition of fatty acid synthase using antitumor antibiotic cerulenin or a synthetic analog C75 markedly increase the malonyl-CoA levels in breast carcinoma cells. On the other hand, the fatty acid synthesis inhibitor, TOFA (5-(tetradecyloxy)-2-furoic acid), which only inhibits at the acetyl-CoA carboxylase (ACC) level, does not show any antitumor activity, while at the same time the malonyl-CoA level is decreased to 60% of the control. It is believed that the increased malonyl-CoA level is responsible for the antitumor activity of these fatty acid synthase inhibitors. Regulating malonyl-CoA levels using MCD inhibitors thus constitutes a valuable therapeutic strategy for the treatment of cancer diseases.

Obesity: It is suggested that malonyl-CoA may play a key role in appetite signaling in the brain via the inhibition of the neuropeptide Y pathway (Loftus et al., *Science* 288: 2379 (2000)). Systemic or intracerebroventricular treatment of mice with fatty acid synthase (FAS) inhibitor cerulenin or C75 led to inhibition of feeding and dramatic weight loss. It is found that C75 inhibited expression of the prophagic signal neuropeptide Y in the hypothalamus and acted in a leptin-independent manner that appears to be mediated by malonyl-CoA. Therefore control of malonyl-CoA levels through inhibition of MCD provides a novel approach to the prophylaxis and treatment of obesity.

The design of MCD inhibitors for the treatment of cardiovascular diseases, diabetes, cancers or obesity has not been reported in the literature. We have now found a novel series of compounds containing hexafluoroisopropanol or trifluoromethyl ketone or similar moieties, members of which are potent inhibitors of MCD. The compounds tested both in vitro and in vivo inhibit malonyl-CoA decarboxylase activities and increase the malonyl-CoA concentration in the body. In addition, by way of example, selected compounds induce a significant increase in glucose oxidation as compared with the control in an isolated perfused rat heart assay (McNeill, *Measurement of Cardiovascular Function*, CRC Press, 1997). Advantageously, preferred compounds such as Compounds 1a of the invention have more profound effects in metabolism shift than the known metabolism modulators such as ranolazine or trimetazidine. The compounds of the invention and pharmaceutical composition containing these compounds are therefore useful in medicine, especially in the prophylaxis, management and treatment of various cardiovascular diseases, diabetes, acidosis, cancers and obesity.

Additionally, these compounds are also useful as a diagnostic tool for diseases associated with MCD deficiency or malfunctions.

SUMMARY OF THE INVENTION

The present invention provides novel compounds as depicted in Formula (I), novel pharmaceutical compositions containing the same and methods for the prophylaxis, management and treatment of metabolic diseases and diseases modulated by MCD inhibition. The compounds of this invention are useful for the prophylaxis, management and treatment of diseases involving in malonyl-CoA regulated glucose/fatty acid metabolism pathways. In particular, these compounds and pharmaceutical compositions containing the same are indicated in the prophylaxis, management and treatment of cardiovascular diseases, diabetes, acidosis, cancers and obesity. In addition to the novel compounds and compositions of this invention, the intermediates and processes useful for the preparation of the compounds of the invention are also included within the scope of this invention.

The present invention also includes within its scope diagnostic methods for the detection of diseases associated with MCD deficiency or malfunctions.

The compounds of the invention are represented by the following general structure (I):

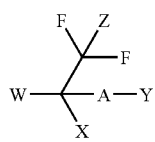
(I)

as well as prodrugs thereof, and pharmaceutically acceptable salts, wherein A, W, X, Y, and Z are as defined below. Other aspects of this invention will become apparent as the description of this invention continues. Hence, the foregoing merely summarizes certain aspects of the invention and is not intended, nor should it be construed, as limiting the invention in any way.

DETAILED DESCRIPTION OF THE INVENTION

The detailed description of the invention that follows is not intended to be exhaustive or to limit the invention to the precise details disclosed. It has been chosen and described to best explain the details of the invention to others skilled in the art.

The novel compounds of the invention are represented by the following general structure (I):

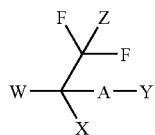
(I)

wherein
W is independently chosen from:
  a five membered substituted non-aromatic heterocyclic ring containing one double bond having the following formulae (I a) and (I b):

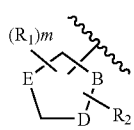
I a

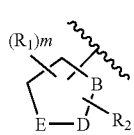
I b wherein B, D and E represent atoms selected from C, N, O or S;
a six membered substituted non-aromatic heterocyclic ring containing zero to two double bonds having the following formulae (I c) and (I d):

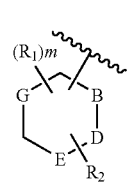
I c

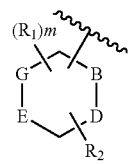
I d wherein B, D, E and G represent atoms selected from C, N, O or S;
an alkynyl group having the following formula (I e):

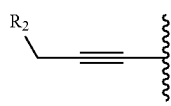
I e a five or six membered substituted aromatic heterocyclic ring having one heteroatom of the following formulae (II a) and (II b):

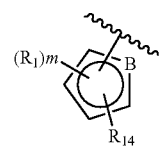
II a

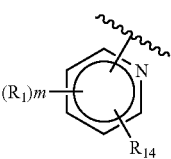
II b a five or six membered substituted aromatic heterocyclic ring having at least two heteroatoms of the formulae (II c), (II d), (II e) and (II f) with the proviso that (II c) and (II d) do not include the pyrazole ring:

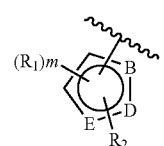
II c

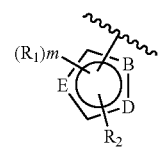
II d

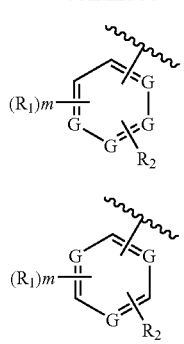

wherein D, E and B represent atoms selected from C, N, O or S, and G represents atoms selected from C or N;

$R_1$ is independently chosen from halo, haloalkyl, hydroxy, thiol, substituted thiol, sulfonyl, sulfinyl, nitro, cyano, amino, substituted amino, $C_1$-$C_6$ alkyl and $C_1$-$C_6$ alkoxy, and when $R_1$ is hydroxy, $C_1$-$C_6$ alkoxy, thiol, substituted thiol, amino, substituted amino, or $C_1$-$C_6$ alkyl, such radical may be combined with $R_2$ or $R_{14}$ to form a ring of 5-7 members when $R_1$ is positioned next to $R_2$ or $R_{14}$;

$R_2$ is selected from —$N(R_3)C(O)R_4$, —$C(O)NR_4R_5$, —$N(R_3)C(O)NR_4R_5$, $N(R_3)SO_2R_7$, —$N(R_3)SO_2NR_4R_3$, —$N(R_3)C(O)OR_4$, —$C(O)OR_4$, —$C(S)OR_4$, —$SR_3$, Phenyl, —$N(R_3)C(S)NR_4R_5$, —$NR_3R_4$, —$N(R_3)C(=NR_3)NR_4R_5$, —$N(R_3)C(=NCN)NR_4R_5$, —$N(R_3)C(=CHNO_2)NR_4R_5$, —$NR_3P(O)R_4R_5$, —$NR_3P(O)(OR_4)(OR_5)$, —$NR_3P(O)(OR_4)(NR_5)$, —$N(R_3)P(O)(NR_4)(NR_5)$, —$N(R_3)C(=NR_3)R_6$, —$COR_6$, —$C(R_6)(OH)R_7$, —$C(R_8)=NOR_4$, —$C(R_8)=NR_3$, —$C(R_8)=NNR_4R_5$, —$SOR_7$, —$SO_2R_7$, —$P(O)(OR_4)(OR_5)$, —$P(O)(R_4)(R_5)$, —$P(O)(OR_4)(OR_5)$—$P(O)(NR_3)(OR_4)$, —$P(O)(NR_4)(NR_5)$, a 3-7 membered ring containing from zero to three heteroatoms selected from O, N, or S, which may be substituted by $R_9$, $R_{10}$, $R_{11}$, $R_{12}$ or $R_{13}$, or may be combined with $R_1$ to form a ring of 5-7 members when $R_1$ is positioned next to $R_2$;

$R_3$ is hydrogen, alkyl, aryl, arylalkyl, heterocyclyl, heterocyclylalkyl, acyl, or may form a ring of 5-7 members with $R_4$ or $R_5$;

$R_4$ is hydrogen, alkyl, aryl, heterocyclyl, acyl, or may form a ring of 5-7 members with $R_5$ or $R_3$;

$R_5$ is hydrogen, alkyl, aryl, or heterocyclyl, acyl or may form a ring of 5-7 members with $R_3$ or $R_4$;

$R_6$ and $R_7$ may be equal or different and are selected from hydrogen, alkyl, aryl, or heterocyclyl;

$R_8$ is hydrogen, alkyl, aryl, heterocyclyl, amino or substituted amino;

$R_9$, $R_{10}$, $R_{11}$ and $R_{12}$ may be equal or different and are selected from hydrogen, alkyl, aryl, heterocyclyl, nitro, cyano, carboxylic acid, ester, amides, halo, hydroxyl, amino, substituted amino, alkoxy, acyl, ureido, sulfonamido, sulfamido, sulfonyl, sulfinyl, or guanadinyl;

$R_{13}$ is hydrogen, alkyl, aryl, ester, heterocyclyl, acyl, sulfonyl, ureido, or guanadinyl;

$R_{14}$ is selected from —$NR_3C(S)NR_4R_5$, —$NR_3C(=NR_3)NR_4R_5$, —$NR_3C(=NCN)NR_4R_5$, —$NR_3C(=CHNO_2)NR_4R_5$, —$NR_3P(O)R_4R_5$, —$NR_3P(O)(OR_4)(OR_5)$, —$NR_3P(O)(OR_4)(NR_5)$, —$NR_3P(O)(NR_4)(NR_5)$, —$NR_3C(=NR_3)R_6$, —$COR_6$, —$C(R_6)(OH)R_7$, —$C(R_8)=NOR_4$, —$C(R_8)=NR_3$, —$C(R_8)=NNR_4R_5$, $SOR_7$, —$SO_2R_7$, —$P(O)(OR_4)(OR_5)$, —$P(O)(R_4)(R_5)$, —$P(O)(OR_4)(OR_5)$, —$P(O)(NR_3)(OR_4)$, —$P(O)(NR_4)(NR_5)$, a 3-7 membered ring containing from zero to three heteroatoms selected from O, N, or S, which may be substituted by $R_9$, $R_{10}$, $R_{11}$, $R_{12}$ or $R_{13}$, or may be combined with $R_1$ to form a ring of 5-7 members when $R_1$ is positioned next to $R_{14}$;

A is O, S, or $NR_3$;

m is from zero to three;

X is H, $CF_2Z$, or $CF_3$, or together with Y forms a double bond when A is O;

Y is hydrogen, or together with X forms a double bond when A is O;

Z is F, Br, Cl, I or $CF_3$;

the corresponding enantiomers, diastereoisomers or tautomers, or a pharmaceutically acceptable salt, or a prodrug thereof in a pharmaceutically-acceptable carrier.

According to the present invention, there are several preferred embodiments which are described more fully below, A preferred embodiment of the present invention relates to those compounds (I) wherein X is $CF_3$; Y is hydrogen; and Z is F.

Another preferred embodiment of the present invention relates to those compounds (I), wherein $R_1$ is hydrogen.

Still another preferred embodiment of the present invention relates to those compounds (I), wherein W is selected from a five or six membered substituted aromatic heterocyclic ring containing one heteroatom and having the following formulae:

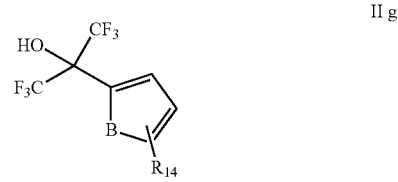

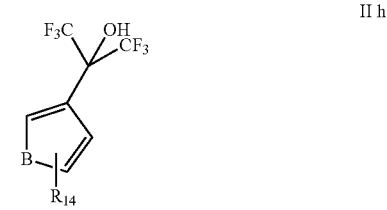

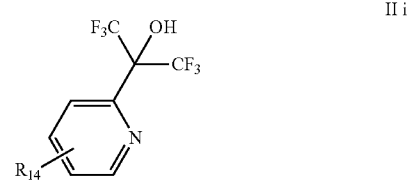

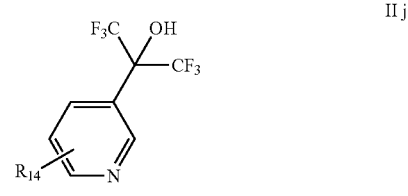

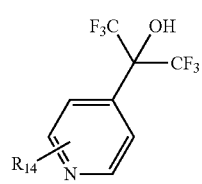

IIk wherein B is selected from N, O or S and $R_{14}$ is as defined above.

Amongst compounds (II g), (II h), (II i), (II j) and (II k), most preferred is pyridyl of the formulae:

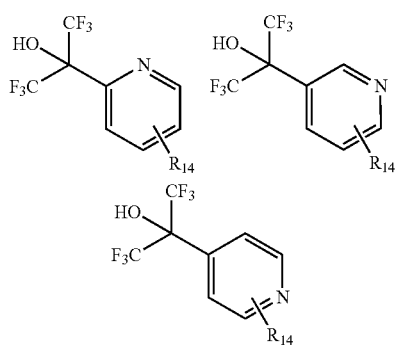

Yet another preferred embodiment of the present invention relates to those compounds (II g), (II h), (II i), (II j) and (II k) wherein $R_{14}$ is selected from the following groups:

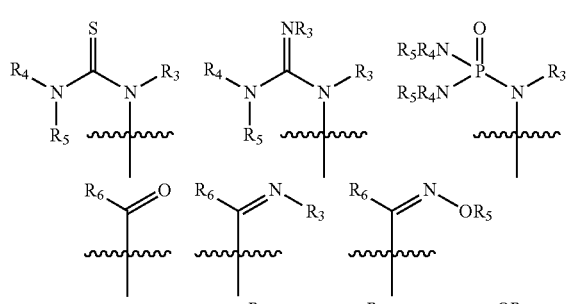

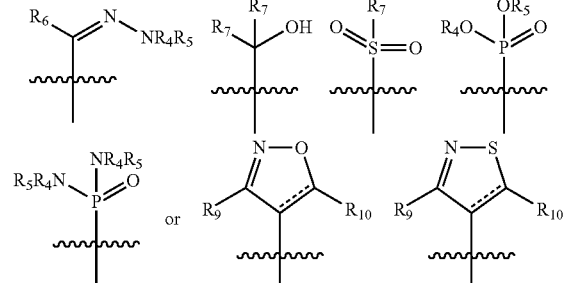

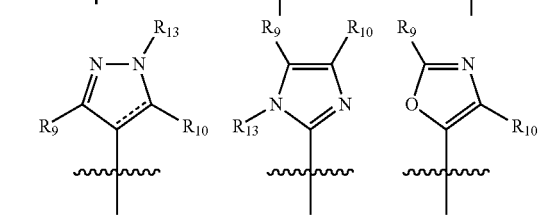

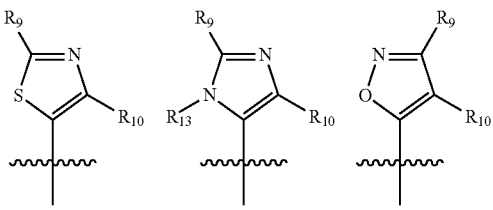

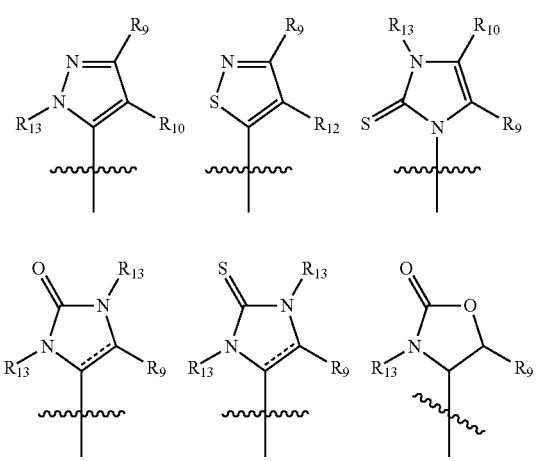

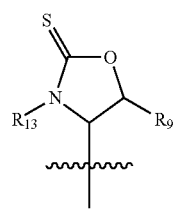

wherein $R_3$, $R_4$, $R_5$, $R_6$, $R_7$, $R_8$, $R_9$, $R_{10}$, $R_{11}$, $R_{12}$ and $R_{13}$ are as defined above.

Still another preferred embodiment of the present invention relates to those compounds (I) wherein W is a five or six membered substituted aromatic heterocyclic ring containing at least two heteroatoms with the proviso that the pyrazole ring is not included and having the following formulae (II m), (II n) and (II o):

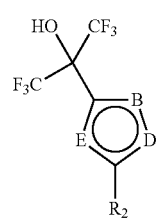

IIm

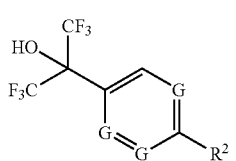

IIn

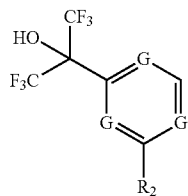

Wherein $R_2$ is as defined as above and D, E and B represent atoms selected from C, N, O or S, and G represents atoms selected from C or N;

Yet another preferred embodiment of the present invention relates to those compounds (II m), (II n) and (II o), wherein $R_2$ is chosen from the following groups:

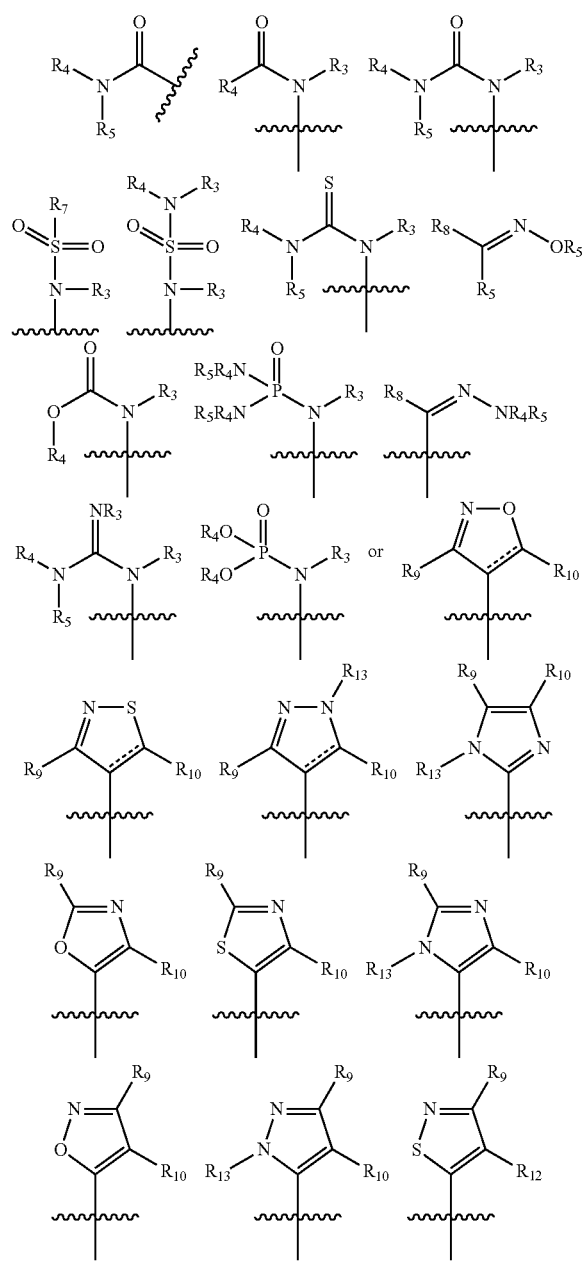

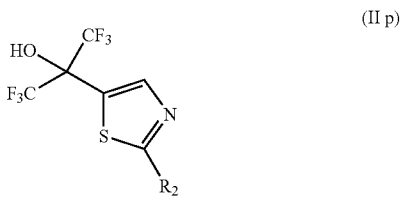

wherein $R_3$, $R_4$, $R_5$, $R_6$, $R_7$, $R_8$, $R_9$, $R_{10}$, $R_{11}$, $R_{12}$ and $R_{13}$ are as defined above.

Amongst compounds (II m), (II n) and (II o) of five or six membered substituted aromatic heterocyclic ring containing at least two heteroatoms, the most preferred for W is a substituted thiazole of the formula (II p):

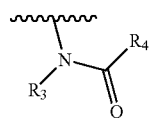

(II p)

In which $R_2$ is more preferably chosen from following group:

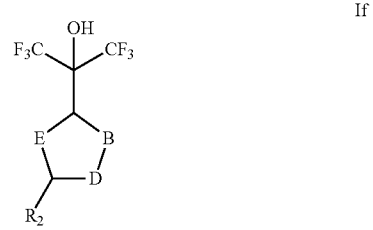

wherein most preferably $R_4$ is chosen from substituted aryl and $R_3$ is chosen from substituted arylalkyl;

Still another preferred embodiment of the present invention relates to those compounds (I), wherein W is chosen from a five membered substituted non-aromatic heterocyclic ring containing one double bond and having the following formula:

If

Wherein at least one of B, D and E represents a heteroatom selected from O, S and N;

Amongst compounds (I f), the preferred five numbered substituted non-aromatic heterocyclic rings have the following formulae:

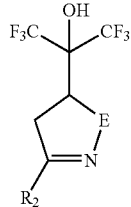
Ig

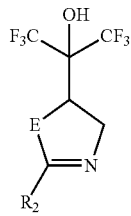
Ih

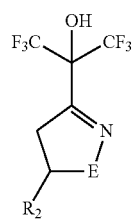
Ii

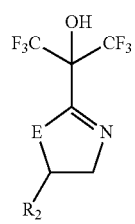
Ij

Amongst above compounds (I g), (I h), (I i) and (I j), a more preferred non-aromatic heterocyclic ring has the following formula, wherein E represents a hetero atom selected from O, S or N:

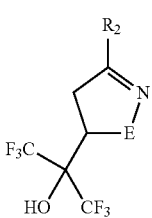
Ik

The most preferred non-aromatic heterocyclic ring has the following formula:

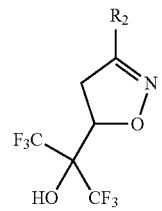
Im wherein $R_2$ is preferably selected from the following groups:

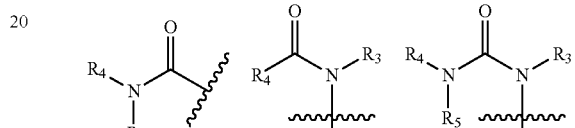

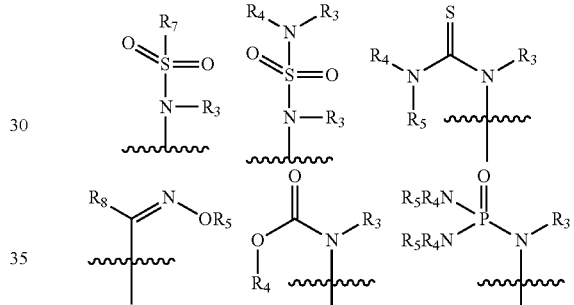

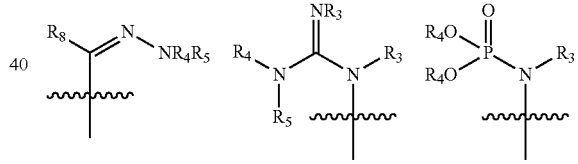

or

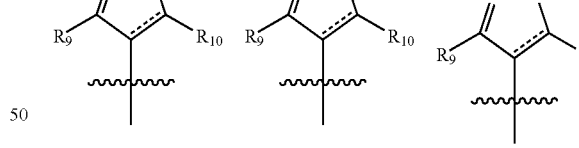

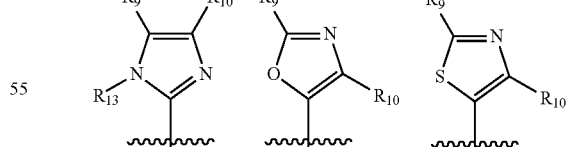

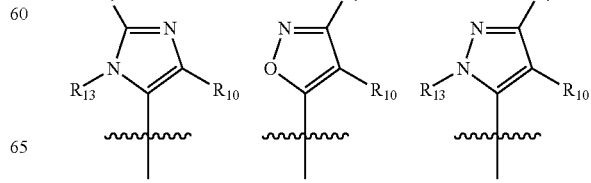

-continued

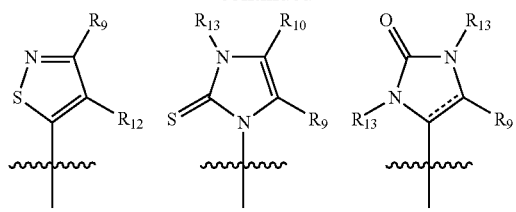

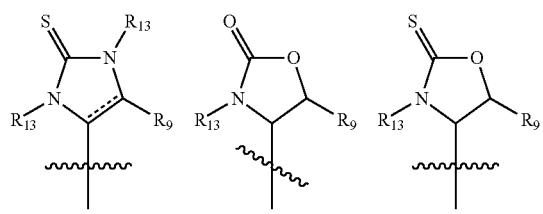

wherein $R_3$, $R_4$, $R_5$, $R_6$, $R_7$, $R_8$, $R_9$, $R_{10}$, $R_{11}$, $R_{12}$ and $R_{13}$ are as defined above.

Amongst above $R_2$ groups of compound (I m), most preferred are the following:

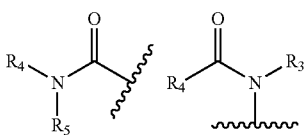

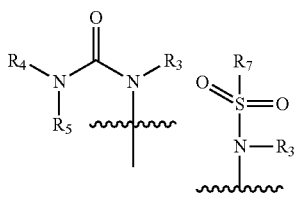

wherein $R_3$, $R_4$, $R_5$, and $R_7$ are as defined above.

Exemplary of the compounds of this invention (I) are:

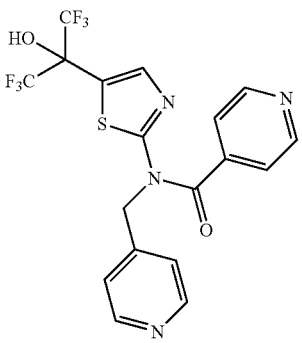

-continued

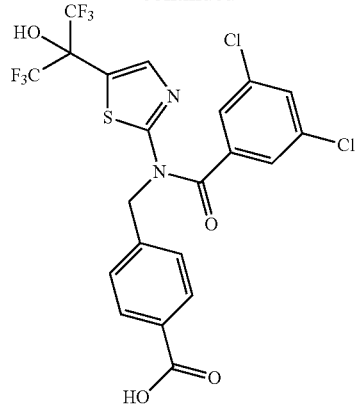

DEFINITIONS

As used herein, "alkyl" means a cyclic, branched, or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 12 carbon atoms, preferably 1 to 10, and more preferably 1 to 8 carbon atoms or cyclic groups containing three to eight carbons.

As used herein, "lower alkyl" means a subset of alkyl, and thus is a hydrocarbon substituent, which is linear, cyclic or branched. Preferred lower alkyls are of 1 to about 6 carbons, and may be branched or linear, and may include cyclic substituents, either as part or all of their structure. Examples of lower alkyl include butyl, propyl, isopropyl, ethyl, and methyl. Likewise, radicals using the terminology "lower" refer to radicals preferably with 1 to about 6 carbons in the alkyl portion of the radical.

As used herein, "amido" means a H—CON— or alkyl-CON—, aryl-CON— or heterocyclyl-CON group wherein the alkyl, aryl or heterocyclyl group is as herein described.

As used herein, "aryl" means a substituted or unsubstituted aromatic radical having a single-ring (e.g., phenyl) or multiple condensed rings (e.g., naphthyl or anthryl), which can be optionally unsubstituted or substituted with amino, cyano, hydroxyl, lower alkyl, haloalkyl, alkoxy, nitro, halo, mercapto, and other substituents, and which may or may not include one or more heteroatoms. Preferred carbocyclic aryl is phenyl. The term "heteroaryl" is clearly contemplated in the term "aryl". Preferably where the term aryl represents a heterocycle, it is referred to as "heteroaryl", and has one or more heteroatom(s). Preferred are monocyclic heterocycles of 5 or 6 members. Hence preferred heteroaryl is a monovalent unsaturated aromatic group having a single ring and having at least one hetero atom, such as N, O, or S, within the ring, which can optionally be unsubstituted or substituted with amino, cyano, nitro, hydroxyl, alkyl, haloalkyl, alkoxy, aryl, halo, mercapto, oxo (hence forming a carbonyl.) and other substituents. Examples of heteroaryl include thienyl, pyridyl, furyl, oxazolyl, oxadiazolyl, pyrolyl, imidazolyl, triazolyl, thiadiazolyl, pyrazolyl, isoxazolyl, thiadiazolyl, pyranyl, pyrazinyl, pyrimidinyl, pyridazinyl, triazinyl, thiazolyl and others.

In this definition it is clearly contemplated that substitution on the aryl ring is within the scope of this invention. Where substitution occurs, the radical is called substituted aryl. Preferably one to three, more preferably one or two, and most preferably one substituent occur on the aryl ring. Preferred substitution patterns in five membered rings are substituted in the 2 position relative to the connection to the claimed molecule. Though many substituents will be useful, preferred substituents include those commonly found in aryl compounds, such as alkyl, hydroxy, alkoxy, cyano, nitro, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, aryl-CO— or heterocyclyl-CO— group wherein the alkyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 5 carbons in length, More preferred haloalkyls are 1 to about 4 carbons, and most preferred are 1 to 3 carbons in length. The skilled artisan will recognize then that as used herein, "haloalkylene" means a diradical variant of haloalkyl, such diradicals may act as spacers between radicals, other atoms, or between the parent ring and another functional group. For example, the linker CHF—CHF is a haloalkylene diradical.

As used herein, "heterocyclyl" means heterocyclic radicals, which are saturated or unsaturated. These may be substituted or unsubstituted, and are attached to other via any available valence, preferably any available carbon or nitrogen. More preferred heterocycles are of 5 or 6 members. In six membered non-aromatic monocyclic heterocycles, the heteroatom(s) are selected from one up to three of O, N or S, and wherein when the heterocycle is five membered and non-aromatic, preferably it has one or two heteroatoms selected from O, N, or S.

As used herein, "substituted amino" means an amino radical which is substituted by one or two alkyl, aryl, or heterocyclyl groups, wherein the alkyl, aryl or heterocyclyl are defined as above.

As used herein, "substituted thiol" means RS— group wherein R is an alkyl, an aryl, or a heterocyclyl group, wherein the alkyl, aryl or heterocyclyl are defined as above.

As used herein, "sulfonyl" means an alkylSO$_2$, arylSO$_2$ or heterocyclyl-SO$_2$ group wherein the alkyl, aryl or heterocyclyl are defined as above.

As used herein, "sulfamido" means an alkyl-N—S(O)$_2$N—, aryl-NS(O)$_2$N— or heterocyclyl-NS(O)$_2$N— group wherein the alkyl, aryl or heterocyclyl group is as herein described.

As used herein, "sulfonamido" means an alkyl-S(O)$_2$N—, aryl-S(O)$_2$N— or heterocyclyl-S(O)$_2$N— group wherein the alkyl, aryl or heterocyclyl group is as herein described.

As used herein, "ureido" means an alkyl-NCON—, aryl-NCON— or heterocyclyl-NCON— group wherein the alkyl, aryl or heterocyclyl group is as herein described A used herein, a "radical" may form a ring with another radical as described herein. When such radicals are combined, the skilled artisan will understand that there are no unsatisfied valences in such a case, but that specific substitutions, for example a bond for a hydrogen, is made. Hence certain radicals can be described as forming rings together. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic or carbocyclic radicals, and such radicals may be saturated, unsaturated, or aromatic. For example, preferred heterocyclic ring systems include heterocyclic rings, such as morpholinyl, piperidinyl, imidazolyl, pyrrolidinyl, and pyridyl.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein. For example,

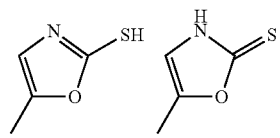

the above substructures clearly represent the same radical and reference to either clearly contemplates the other. In addition, the following compounds may represent prodrugs when R can be removed by biological processes in situ:

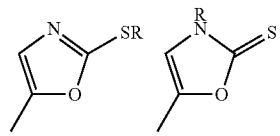

Compounds and compositions herein also specifically contemplate pharmaceutically acceptable salts, whether cationic or anionic. A "pharmaceutically-acceptable salt" is an anionic salt formed at any acidic (e.g., carboxyl) group, or a cationic salt formed at any basic (e.g., amino) group. Many such salts are known in the art, as described in World Patent Publication 87/05297, Johnston et al., published Sep. 11, 1987 (incorporated by reference herein). Preferred counterions of salts formable at acidic groups can include cations of salts, such as the alkali metal salts (such as sodium and potassium), and alkaline earth metal salts (such as magnesium and calcium) and organic salts. Preferred salts formable at basic sites include anions such as the halides (such as chloride salts). Of course, the skilled artisan is aware that a great number and variation of salts may be used, and examples exist in the literature of either organic or inorganic salts useful in this manner.

It is also clearly contemplated that compounds of the invention can be provided as biohydrolyzable prodrugs, as they are understood in the art. "Prodrug", as used herein is any compound wherein when it is exposed to the biological processes in an organism, is hydrolyzed, metabolized, derivatized or the like, to yield an active substance having the desired activity. The skilled artisan will recognize that prodrugs may or may not have any activity as prodrugs. It is the intent that the prodrugs described herein have no deleterious effect on the subject to be treated when dosed in safe and effective amounts. These include for example, biohydrolyzable amides and esters. A "biohydrolyzable amide" is an amide compound which does not essentially interfere with the activity of the compound, or that is readily converted in vivo by a cell, tissue, or human, mammal, or animal subject to yield an active compound of the invention. A "biohydrolyzable ester" refers to an ester compound of the invention that does not interfere with the activity of these compounds or that is readily converted by an animal to yield an active formula (I) compound. Such biohydrolyzable prodrugs are understood by the skilled artisan and are embodied in regulatory guidelines.

Inasmuch as the compounds of the invention may contain optical centers, "optical isomer", "stereoisomer", "enantiomer," "diastereomer," as referred to herein have the standard art recognized meanings (cf. *Hawleys Condensed Chemical Dictionary*, 11th Ed.) and are included in the compounds claimed, whether as racemates, or their optical isomers, stereoisomers, enantiomers, diastereomers.

As used herein "cardiovascular diseases" include arrhthymia, atrial fibrillation, congestive heart failure, coronary artery disease, hypertension, myocardial infarction, stroke, ventricular fibrillation, among others, particularly cardiovascular ischemia such as angina pectoris and those conditions treatable by shifting metabolism within the cardiovascular system.

As used herein, the term "metabolic disease", means disorders in a mammal in which errors of metabolism, imbalances in metabolism, or sub-optimal metabolism occur. The metabolic diseases as used herein also contemplate a disease that can be treated through the modulation of metabolism, although the disease itself may or may not be caused by specific metabolism blockage. Particularly, such metabolic disease involves glucose and fatty acid oxidation pathway. Still more particularly, such metabolic disease involves MCD or is modulated by levels of Malonyl CoA. All these conditions are collectively referred to herein as an "MCD or MCA related disorder."

Compositions

The compositions of the present invention comprise:
(a) a safe and effective amount of an MCD inhibiting compound (I), prodrug or pharmaceutical salt thereof; and
(b) a pharmaceutically-acceptable carrier.

As discussed above, numerous diseases can be mediated by MCD related therapy. Thus, the compounds of this invention are useful in therapy with regard to conditions involving this MCD activity.

Accordingly, the compounds of this invention can therefore be formulated into pharmaceutical compositions for use in prophylaxis, management and treatment of these conditions. Standard pharmaceutical formulation techniques are used, such as those disclosed in Remington's Pharmaceutical Sciences, Mack Publishing Company, Easton, Pa.

A "safe and effective amount" of a compound of the present invention is an amount that is effective, to inhibit MCD at the site(s) of activity, in a subject, a tissue, or a cell, and preferably in an animal, more preferably in a mammal, without undue adverse side effects (such as toxicity, irritation, or allergic response), commensurate with a reasonable benefit/risk ratio, when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4. In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a compound that is suitable for administration to an animal, preferably mammal subject, in a single dose, according to good medical practice. (The preparation of a single or unit dosage form however, does not imply that the dosage form is administered once per day or once per course of therapy. Such dosage forms are contemplated to be administered once, twice, thrice or more per day, and are expected to be given more than once during a course of therapy, though a single administration is not specifically excluded. The skilled artisan will recognize that the formulation does not specifically contemplate the entire course of therapy and such decisions are left for those skilled in the art of treatment rather than formulation.) These compositions preferably contain from about 5 mg (milligrams), more preferably from about 10 mg to about 1000 mg, more preferably to about 500 mg, most preferably to about 300 mg, of the selected compound.

The compositions of this invention may be in any of a variety of forms, suitable (for example) for oral, nasal, rectal, topical (including transdermal), ocular, intracerebrally, intravenous, intramuscular, or parenteral administration. (The skilled artisan will appreciate that oral and nasal compositions comprise compositions that are administered by inhalation, and made using available methodologies.) Depending upon the particular route of administration desired, a variety of pharmaceutically-acceptable carriers well-known in the art may be used. These include solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct application or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the compound. Suitable carriers for topical administration preferably remain in place on the skin as a continuous film, and resist being removed by perspiration or immersion in water. Generally, the carrier is organic in nature and capable of having dispersed or dissolved therein the compound. The carrier may include pharmaceutically-acceptable emollients, emulsifiers, thickening agents, solvents and the like.

Methods of Administration

The compounds and compositions of this invention can be administered topically or systemically. Systemic application includes any method of introducing compound into the tissues of the body, e.g., intra-articular, intrathecal, epidural, intramuscular, transdermal, intravenous, intraperitoneal, subcutaneous, sublingual administration, inhalation, rectal, or oral administration. The compounds of the present invention are preferably administered orally.

The specific dosage of the compound to be administered, as well as the duration of treatment is to be individualized by the treating clinicians. Typically, for a human adult (weighing approximately 70 kilograms), from about 5 mg, preferably from about 10 mg to about 3000 mg, more preferably to about 1000 mg, more preferably to about 300 mg, of the selected compound is administered per day. It is understood that these dosage ranges are by way of example only, and that daily administration can be adjusted depending on the factors listed above.

In all of the foregoing, of course, the compounds of the invention can be administered alone or as mixtures, and the compositions may further include additional drugs or excipients as appropriate for the indication. For example, in the treatment of cardiovascular diseases, it is clearly contemplated that the invention may be used in conjunction with beta-blockers, calcium antagonists, ACE inhibitors, diuretics, angiotensin receptor inhibitors, or known cardiovascular drugs or therapies. Hence, in this example, novel compounds or compositions of this invention are useful when dosed together with another active and can be combined in a single dosage form or composition.

The composition can also be administered in the form of liposome delivery system, such as small unilamellar vesicles, large unilamellar vesicles, and mutilamellar vesicles. Liposomes can be formed from a variety of phospholipids, such as cholesterol, stearylamine, or phosphayidylcholines.

Preparation of Compounds of the Invention

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the claimed compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March *Advanced Organic Chemistry* (Wiley), Carey and Sundberg, *Advanced Organic Chemistry* and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, $2^{nd}$ Ed., John Wiley & Sons (1991).

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure.

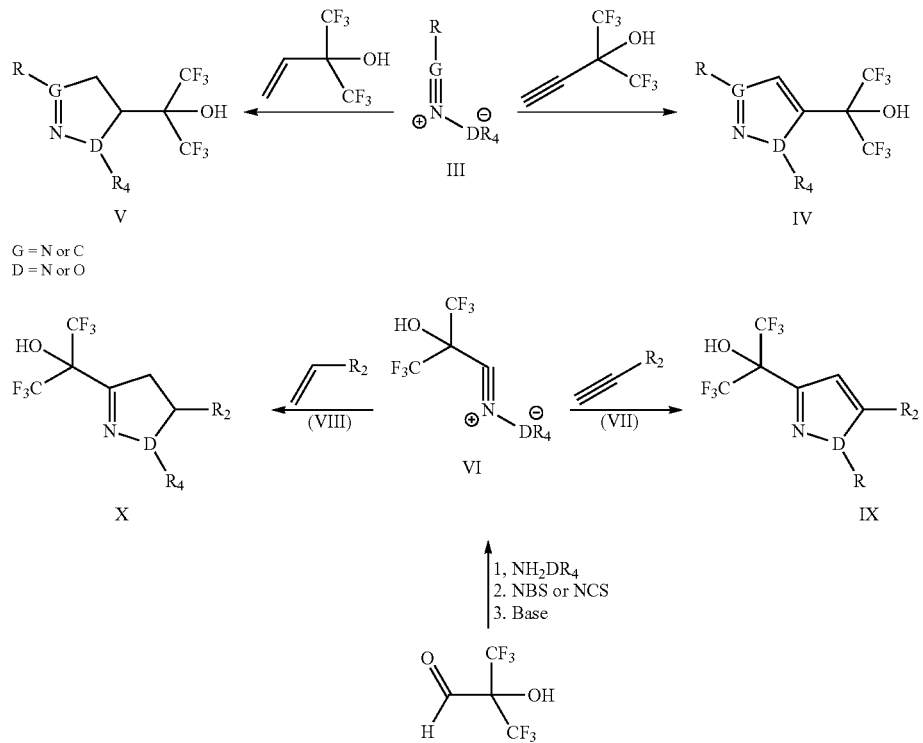

Scheme 1a

Scheme 1b

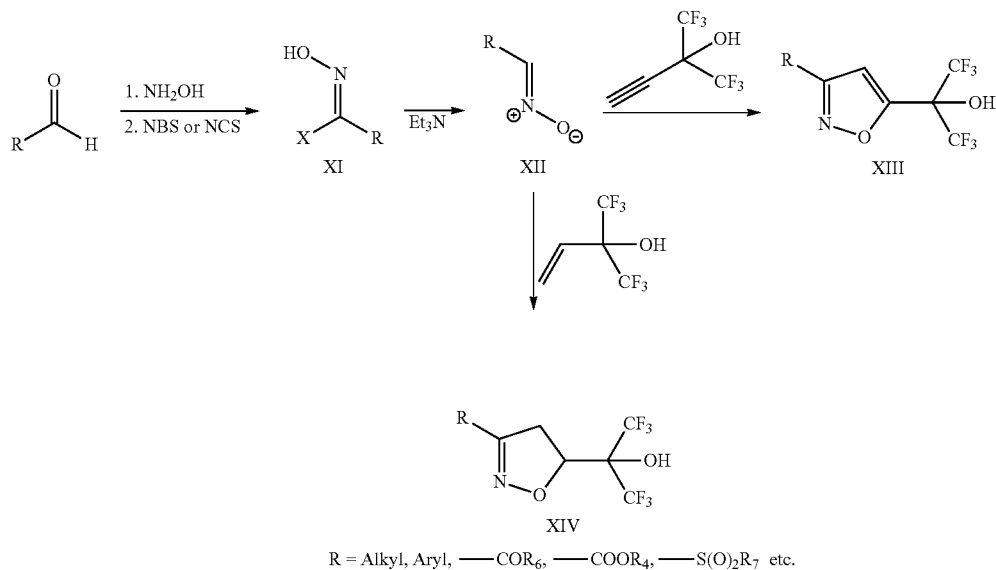

R = Alkyl, Aryl, —COR$_6$, —COOR$_4$, —S(O)$_2$R$_7$ etc.

when R = COOH

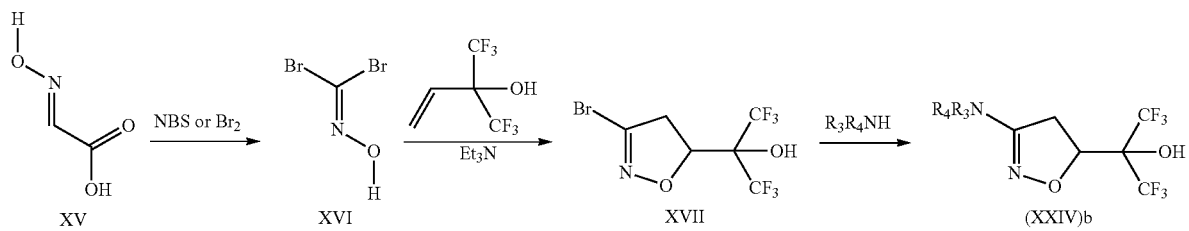

As shown in Scheme 1a, the 1,3-dipolar cycloaddition of dipoles (III) with 1,1,1-trifluoro-2-trifluoromethyl-but-3-yn-2-ol or 1,1,1-trifluoro-2-trifluoromethyl-but-2-en-2-ol can afford relevant hexafluoroisopropanol derivatives of five membered heterocycles (IV) or (V).

Alternatively hexafluoroisopropanol derivatives of five membered heterocycles (IX) or (X) can be synthesized from the cycloaddition of dipoles containing hexafluoroisopropanol (VI) with alkynes (VII) or alkenes (VIII).

For example (Scheme 1b), cycloaddition of nitrile oxides (XII) with 1,1,1-trifluoro-2-trifluoromethyl-but-3-yn-2-ol or 1,1,1-trifluoro-2-trifluoromethyl-but-2-en-2-ol provides respectively the hexafluoroisopropanol derivatives of isoxazole (XIII) or isoxazoline (XIV). The nitrile oxide (XII) can be formed in situ from an aldoxime (XI), which is prepared from the condensation of aldehyde with hydroxyamine, by treatment with a chlorinating or brominating agent and a weak base. However bromination of hydroxyimino-acetic acid (XV) affords hydroxy-carbonimidic acid dibromide (XVI) which reacts with (II) to provide 2-(3-bromo-4,5-dihydro-isoxazol-5-yl)-1,1,1,3,3,3-hexafluoro-propan-2-ol (XVII). Reaction of (XVII) with alkylamines gives rise to corresponding alkylaminoderivatives (XXIV)b.

Scheme 2

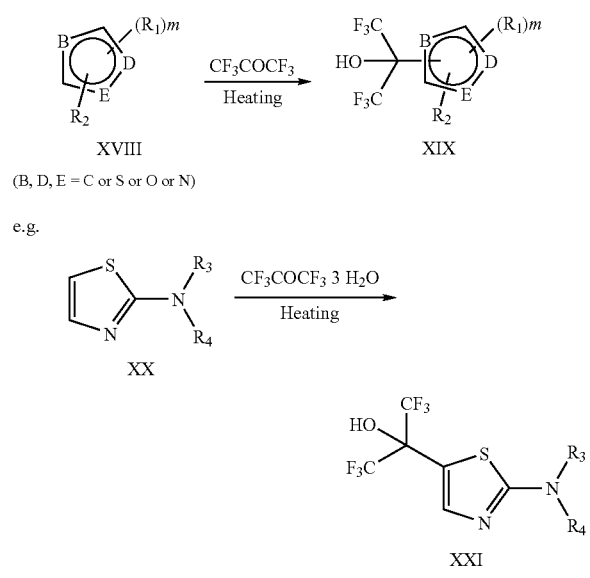

(B, D, E = C or S or O or N)

e.g.

Scheme 2 describes a method for preparation of hexafluoroisopropanol derivatives (XIX) by reacting aromatic heterocycles (XVIII) with hexafluoroacetone. For instance, reaction of 2-alkylamino-1,3-thiazoles or amino-1,3-thiazoles (XX) with hexafluoroacetone hydrate under heating conditions yields the hexafluoroisopropanol derivatives of 1,3-thiazole (XXI).

Hexafluoroisopropanol derivatives of five membered aromatic or non aromatic heterocyclic rings (XXIV), for example 2-N-alkylthiazolyl-hexafluoroisopropanol (XXIV) a, or 1,1,1,3,3,3-Hexafluoro-2-(3-alkylamino-4,5-dihydro-isoxazol-5-yl)-propan-2-ol (XXIV)b, are converted into the corresponding amides (XXV), amidophsphates (XXVI), sulfonamides (XXVII), ureas (XXVIII), carbamates (XXV,

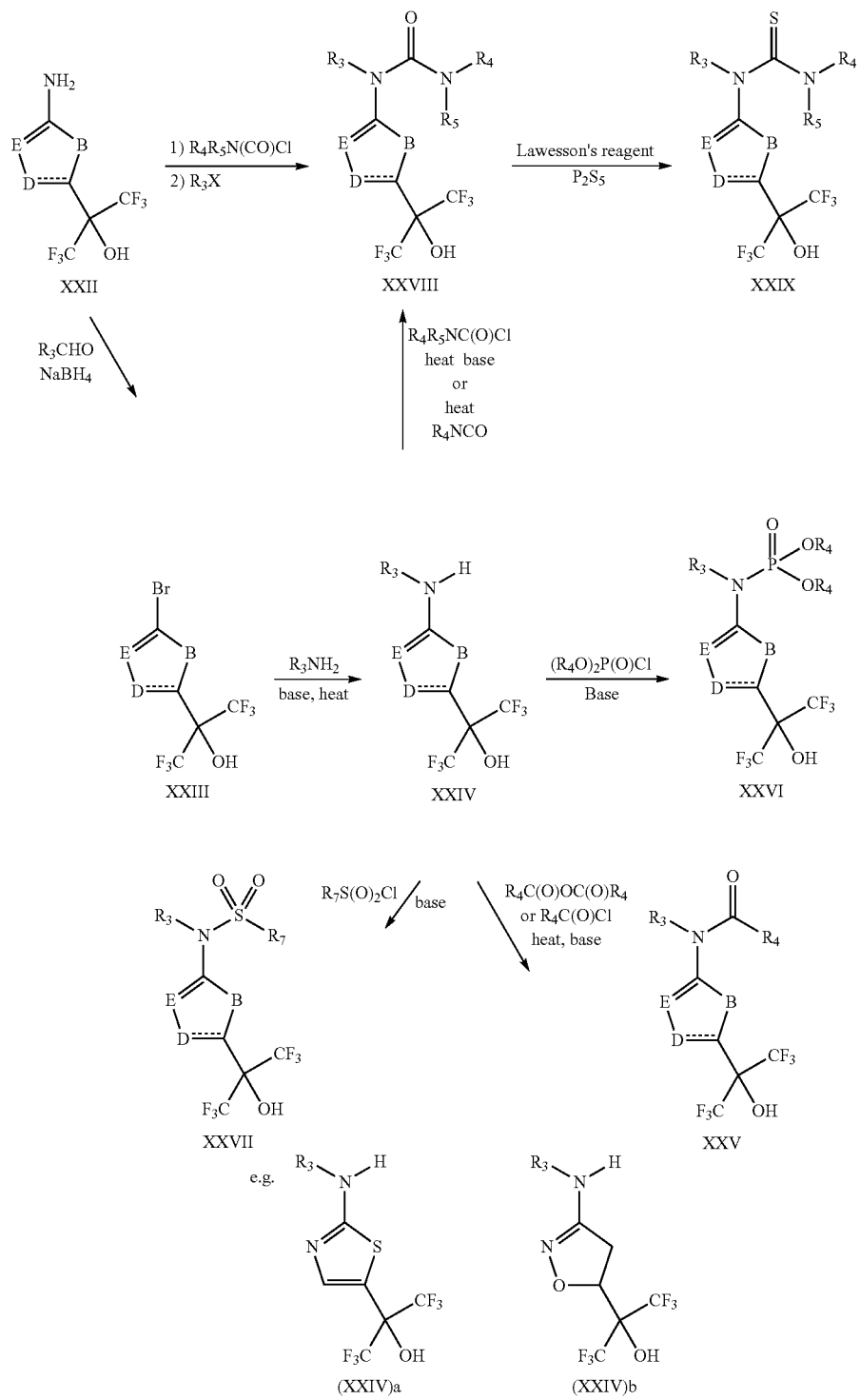

$R_4$=$OR_3$) and thioureas (XXIX) under reaction conditions depicted in Scheme 3.

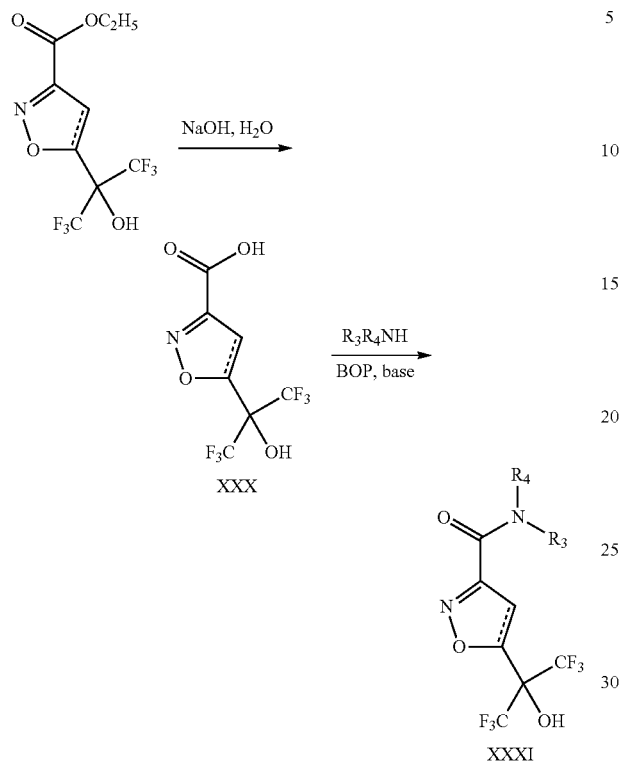

As shown in scheme 4, amide derivatives of isoxazoline or isoxazole (XXXI) are prepared from the coupling of acid derivatives (XXX) with amines in the presence of a coupling reagent such as (benzotriazol-1-yloxy)tris(dimethylamino) phosphonium hexafluorophosphate (Bop) and a base.

As shown in scheme 5, under depicted reaction conditions, alcohol (XXXIV), hydrazone (XXXV), and oxime (XXXVI) derivatives of isoxazoline or isoxazole can be prepared via a common ketone/aldehyde intermediate (XXXIII), which is prepared from 1,3-dipolar reaction of the relevant nitrile oxide (XXXII) with 1,1,1-trifluoro-2-trifluoromethyl-but-3-yn-2-ol or 1,1,1-trifluoro-2-trifluoromethyl-but-2-en-2-ol.

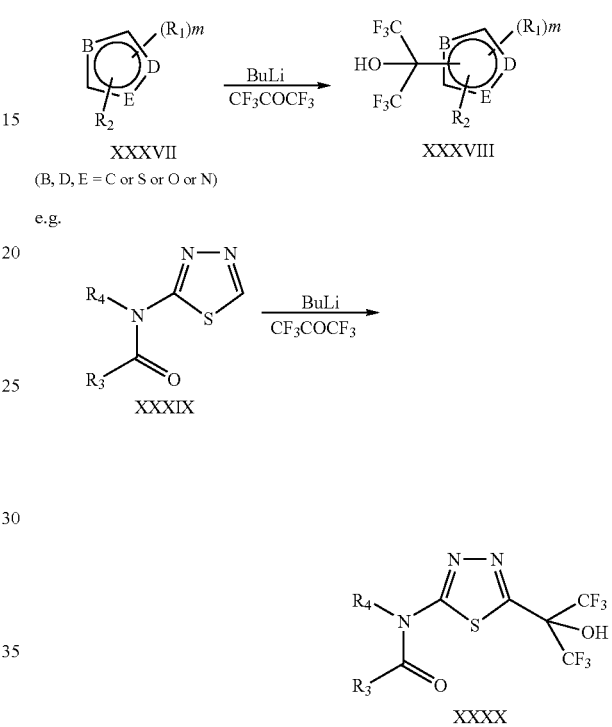

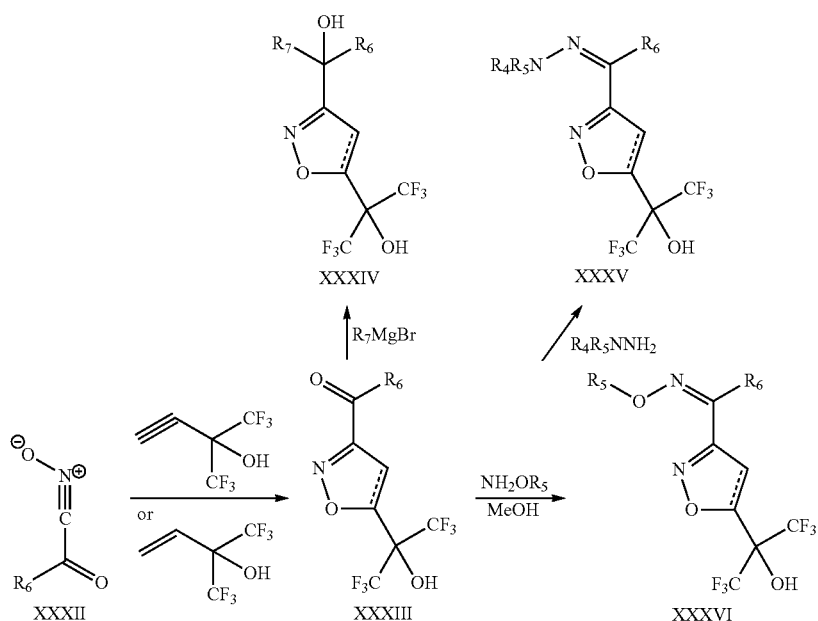

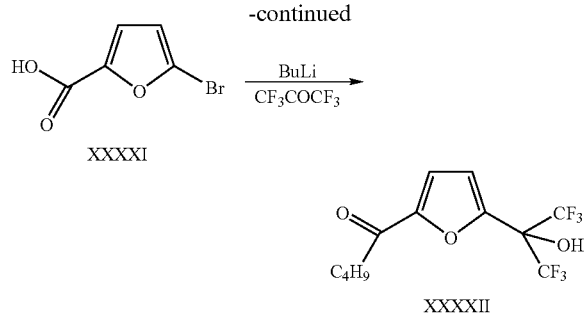

XXXXI

XXXXII

In Scheme 6 an alternative approach to the hexafluoroisopropanol derivatives (XXXVIII) of five membered aromatic heterocyclic rings involves the reaction of hexafluoroacetone with organometallic compounds, which can be formed from (XXXVII). Thus lithiation of intermediates (XXXIX), which are prepared by the reaction of commercially available 2-alkylamino-thiadiazole with acid chlorides, followed by the addition of hexafluoroacetone, gives the desired hexafluoroisopropanol derivatives (XXXX). On the other hand, reaction of 5-bromo-2-furoic acid (XXXXI) with excess amount of n-butyl lithium followed by the treatment with hexafluoroacetone provides 1-{5-[2,2,2-trifluoro-1-hydroxy-1-(trifluoromethyl)ethyl]furan-2-yl}pentan-1-one (XXXXII).

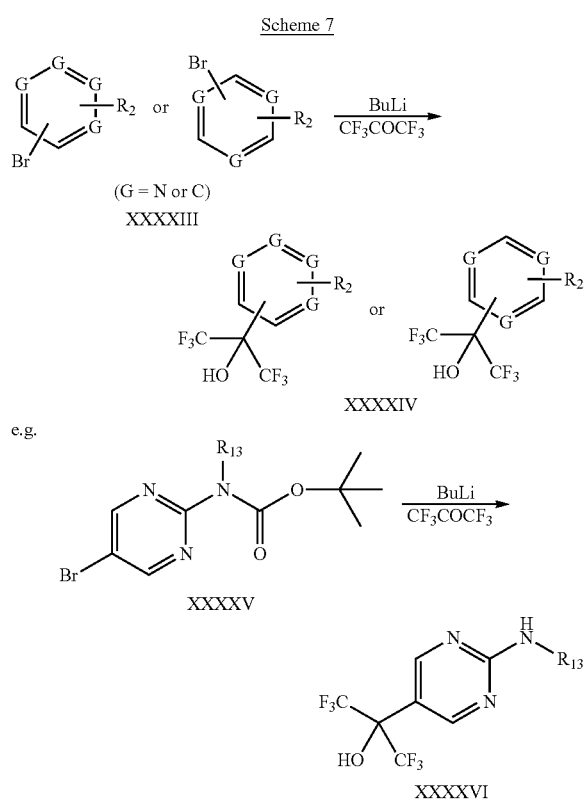

The hexafluoroisopropanol derivatives (XXXXIV) of six membered heterocyclic rings containing one to four nitrogen atoms can be prepared by the method presented in Scheme 7. Thus treatment of 5-bromo-2-aminopyrimidine derivative (XXXXV) with n-butyllithium results in halogen-lithium exchange and subsequent reaction of the corresponding lithium intermediate with hexafluoroacetone affords hexafluoroisopropanol pyrimidine derivative (XXXXVI).

Scheme 8

XXXXI

XXXXII

Scheme 8 depicts the method of synthesis of alkynyl hexafluoroisopropanol derivatives. For example, reaction of hexafluoroacetone with alkynyl lithiums (XXXXVII), prepared by the treatment of alkynes with n-butyl lithium, gives rise to alkynyl hexafluoroisopropanol derivatives (XXXXVIII).

Biological Activity

In Vitro MCD inhibitory assay:

A spectrophotometric method for the determination of malonyl-CoA decarboxylase activity assay described in the literature, is adapted and modified for MCD inhibitory activity assay in a high-throughput format (Kolattukudy et al., *Methods in Enzymology* 71:150 (1981)). The following reagents are added into a 96 well titer plate: Tris-HCl buffer, 20 µL; DTE, 10 µL; 1-malate, 20 µL; NAD, 10 µL; NADH, 25 µL; water, 80 µL; malic dehydrogenase, 5 µL. The contents are mixed and incubated for 2 min followed by the addition of 5 µL of citrate synthase. The compound is added followed by 5 µL of malonyl-CoA decarboxylase prepared from rat heart and 20 µL of malonyl-CoA. The content is incubated and absorbence at 460 nM is measured.

Active compounds are characterized by the concentration of the compound that caused 50% inhibition of MCD activity ($IC_{50}$). The preferred compounds have the $IC_{50}$ value less than 10 µM. The most preferred compounds have the $IC_{50}$ value less than 100 nM.

TABLE I $IC_{50}$ of the MCD inhibitors

| Compound | $IC_{50}$ (µM) |
| --- | --- |
| Example 1-2-1 | 0.024 |
| Example 1-2-2 | 0.177 |
| Example 1-3-1 | 0.213 |
| Example 1-4 | 0.463 |
| Example 3 | 0.124 |
| Example 4 | 2.748 |
| Example 7-1 | 0.739 |
| Example 8-3-1 | 0.060 |
| Example 8-3-3 | 0.127 |
| Example 9-2 | 3.71 |
| Example 11-1 | 0.388 |

Glucose Oxidation and Fatty Acid Oxidation Measurement in the Perfused Rat Heart:

Isolated working hearts from male Sprague-Dawley rats are subjected to a 60-minute aerobic perfusion period with a modified Krebs-Henseleit solution containing 5 mmol/L glucose; 100 µU/mL insulin; 3% BAS; and 1.2 mmol/L palmitate. Working hearts are used in these studies to approximate the metabolic demand of the heart seen in vivo. (Kantor et al., *Circulation Research* 86:580-588 (2000)). The test compound is added 5 minutes into the perfusion period.

Glucose oxidation rates are determined by the quantitative collection of $^{14}CO_2$ produced by hearts perfused with buffer containing [U14]-Glucose. Rates of fatty acid oxidation are determined by the quantitative collection of $^{14}CO_2$ produced by hearts perfused with buffer containing [$^{14}C$]palmitate (McNeill, J. H. in "*Measurement of cardiovascular function*", chapter 2, CRC press, New York (1997)).

Active compounds are characterized by an increase in glucose oxidation as compared to control experiment (DMSO). The compounds that caused statistically significant increases in glucose oxidation are considered to be active. The preferred compounds cause statistically significant increases in glucose oxidation at 20 μM. Statistical significance was calculated using the Student's t test for paired or unpaired samples, as appropriate. The results with P<0.05 are considered to be statistically significant.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) is measured in CDCl$_3$ or other indicated solvents on a Varian NMR spectrometer (Unity Plus 400, 400 MHz for $^1$H) unless otherwise indicated and peak positions are expressed in parts per million (ppm) downfield from tetramethylsilane. The peak multiplicities are denoted as follows, s, singlet; d, doublet; t, triplet; m, multiplet.

The following abbreviations have the indicated meanings:
Bn=benzyl
DMAP=4-(dimethylamino)-pyridine
DMF=N,N-dimethylformamide
DMSO=dimethylsulfoxide
ESIMS=electron spray mass spectrometry
Et$_3$N=triethylamine
EtOAc=ethyl acetate
Lawesson's reagent=2,4-bis(4-methoxyphenyl)-1,3,2,4-dithiadiphosphetane-2,4-disulfide
MgSO$_4$=magnesium sulfate
NaHCO$_3$=sodium bicarbonate
NBS=N-bromosuccinimide
NCS=N-chlorosuccinimide
NH$_4$Cl=ammonium chloride
Ph=phenyl
Py=pyridyl
r.t.=room temperature
THF=tetrahydrofuran
TLC=thin layer chromatography
Alkyl group abbreviations
Me=methyl
Et=ethyl
n-Pr=normal propyl
i-Pr=isopropyl
c-Pr=cyclopropyl
n-Bu=normal butyl
i-Bu=isobutyl
t-Bu=tertiary butyl
s-Bu=secondary butyl
c-Hex=cyclohexyl

Example 1-1-1

Preparation of 2-methyl-N-{5-[2,2,2-trifluoro-1-hydroxy-1-(trifluoromethyl)ethyl]-1,3-thiazol-2-yl}propanamide

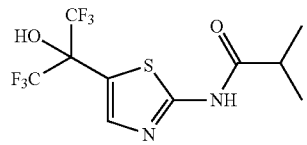

Step 1

Preparation of 2-(2-amino-1,3-thiazol-5-yl)-1,1,1,3,3,3-hexafluoropropan-2-ol

A catalytic amount of molecular sieves powder (4A) was added to a mixture of 2-aminothiazole 200 mg (2 mmol) and hexafluoroacetone trihydrate (880 mg, 4 mmol). The mixture was heated at 100° C. for 8 h. Ethyl acetate was added and the mixture was filtered. Organic solvents were evaporated under reduced pressure. The residue was recrystallized in THF and hexanes to afford the title product (389 mg) as a white solid. $^1$H NMR (DMSO-d6) δ7.12 (s, 1H), 7.45 (brs, 2H), 8.85 (s, 1H); ESIMS: m/z 267 (M+H).

Step 2

To a solution of 2-(2-amino-1,3-thiazol-5-yl)-1,1,1,3,3,3-hexafluoropropan-2-ol (267 mg, 1 mmol) obtained above in triethylamine (150 mg, 1.49 mmol) and THF (10 ml), was added isobutyryl chloride (110 mg 1.03 mmol) at room temperature. The reaction mixture was stirred for 30 minutes. Solvent was removed under reduced pressure and the residue was dissolved in EtOAc. The organic layer was washed with water and brine, dried (MgSO$_4$) and concentrated. The residue was recrystallized in THF and hexanes to afford the title compound (282 mg) as a white solid. $^1$H NMR (DMSO-d6) δ1.08 (d, 6H), 2.72 (m, 1H), 7.60 (s, 1H), 9.10 (brs, 1H), 12.3 (brs, 1H); ESIMS: 319 (M−OH).

TABLE 2

The following compounds are prepared in accordance with the procedure described in the example 1-1-1.

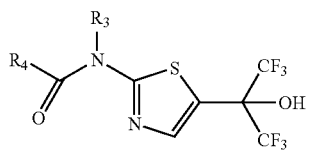

| Example | R$_3$ | R$_4$ |
|---|---|---|
| Example 1-1-1 | H | i-Pr- |
| Example 1-1-2 | H | PhCH$_2$CH$_2$— |
| Example 1-1-3 | H | Ph- |

Example 1-2-1

Preparation of N-(pyridin-4-ylmethyl)-N-{5-[2,2,2-trifluoro-1-hydroxy-1-(trifluoromethyl)ethyl]-1,3-thiazol-2-yl}pyridine-4-carboxamide

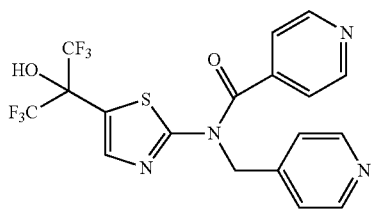

Step 1

Preparation of 1,1,1,3,3,3-hexafluoro-2-{2-[(pyridin-4-ylmethyl)amino]-1,3-thiazol-5-yl}propan-2-ol A mixture of 2-aminothiazole (3 g, 30 mmol) and 4-pyridinecarboxaldehyde (3.21 g, 30 mmol) in toluene (50 ml) was refluxed with a Dean-Stark water separator for 3 h. Solvent was removed under reduced pressure and the resulting yellow solid was dissolved in $CH_3OH$ (80 ml). The solution was carefully treated with sodium borohydride (1.8 g) and was stirred for 20 minutes. The reaction mixture was quenched with 1N NaOH and evaporated to dryness. The residue was dissolved in EtOAc, washed with brine and dried ($MgSO_4$). Solvent was evaporated to give the crude intermediate N-(pyridin-4-ylmethyl)-1,3-thiazol-2-amine as a brown solid (4.2 g).

Molecular sieves powder (4A) (1 g) was added to a mixture of crude intermediate N-(pyridin-4-ylmethyl)-1,3-thiazol-2-amine prepared above (2.5 g 13 mmol) and hexafluoroacetone trihydrate (4 g, 18.1 mmol) in benzene (3 ml). The mixture was heated at 80° C. for 24 h. Acetonitrile was added and mixture was filtered. Solvent was evaporated under reduced pressure. The residue was chromatographed on silica gel, eluting with a 95:5 mixture of $CHCl_3$ and $CH_3OH$, to afford the title compound as an orange solid (1.1 g). $^1H$ NMR (DMSO-d6) δ 4.3 (d, 2H), 7.10 (s, 1H), 7.42 (d, 2H); 7.78 (d, 2H), 8.45 (brs, 1H), 8.82 (brs, 1H); ESIMS: m/z 356 (M−H).

Step 2

To a solution of 1,1,3,3,3-hexafluoro-2-{2-[(pyridin-4-1yl-methyl)amino]-1,3-thiazol-5-yl}propan-2-ol (714.5 mg, 2 mmol) obtained from step 1 in dioxane (8 ml) was added isonicotinic anhydride (912 mg, 4 mmol). The reaction mixture was refluxed at 100° C. for 2 h and then concentrated under reduced pressure. The residue was extracted with EtOAc (3×100 ml). The organic layer was washed with $H_2O$ (3×40 ml) and dried over $MgSO_4$. Solvent was evaporated to give a residue which was purified by recrystallization from ethyl acetate and hexanes to afford the title compound as a light yellow solid (528 mg). (DMSO-d6) δ5.28 (s, 2H), 7.12 (d, 2H), 7.49 (d, 2H), 7.72 (s, 1H), 8.42 (d, 2H) 8.65 (d, 2H); 9.3 (brs, 1H); ESIMS: m/z 461 (M−H).

TABLE 3

The following compounds are prepared in accordance with the procedure described in the above example 1-2-1.

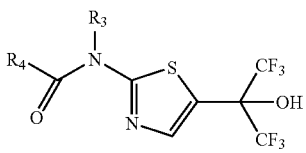

| Example | R3 | R4 |
|---|---|---|
| Example-1-2-1 | 4-Py-$CH_2$— | Py- |
| Example-1-2-2 | n-Bu- | $CH_3$— |
| Example-1-2-3 | n-Bu- | iPr- |
| Example-1-2-4 | 2-Furanyl-$CH_2$— | i-Pr- |
| Example-1-2-5 | 3-Py-$CH_2$— | iPr- |
| Example-1-2-6 | n-Bu- | 4-Py- |
| Example-1-2-7 | 4-Py-$CH_2$— | i-Pr |
| Example-1-2-8 | 2-Py-$CH_2$— | i-Pr- |
| Example-1-2-9 | n-Bu- | n-Pr- |
| Example-1-2-10 | Bn- | i-Pr- |
| Example-1-2-11 | n-Bu- | Ph- |
| Example-1-2-12 | 4-Py-$CH_2$— | $CH_3$— |
| Example-1-2-13 | Et- | i-Pr- |
| Example-1-2-14 | Et- | $CH_3$— |
| Example-1-2-15 | 4-Cyano-Bn- | $CH_3$— |
| Example-1-2-16 | 4-Cyano-Bn- | —CH(Ph)$CH_2CO_2H$ |
| Example-1-2-17 | 4-Cyano-Bn- | i-Pr- |
| Example-1-2-18 | 2-(1-Methyl-1H-imidazolyl)-$CH_2$ | I-Pr- |
| Example-1-2-19 | 2-Thiazolyl-$CH_2$— | i-Pr- |
| Example-1-2-20 | 4-MeO(O)C-Bn- | i-Pr- |
| Example-1-2-21 | 4-Chloro-Bn- | i-Pr- |
| Example-1-2-22 | 4-HO(O)C-Bn- | i-Pr- |

TABLE 3-continued

The following compounds are prepared in accordance with the procedure described in the above example 1-2-1.

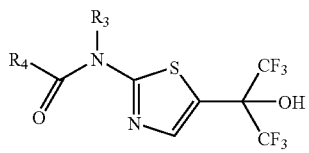

| Example | R₃ | R₄ |
|---|---|---|
| Example-1-2-23 | 3,4-Dichloro-Bn- | I-Pr- |
| Example-1-2-24 | 4-(5H-tetrazol-5-yl)-Bn- | i-Pr- |
| Example-1-2-25 | 4-Methanesulfonyl-Bn- | i-Pr- |
| Example-1-2-26 | 4-(2-Carboxy-vinyl)-Bn- | i-Pr- |
| Example-1-2-27 | 4-Methoxy-Bn- | i-Pr- |
| Example-1-2-28 | 4-Cyano-Bn- | 4-Py- |
| Example-1-2-29 | 4-Cyano-Bn- | —CH₂CH₂C(CH₃)₂CO₂H |
| Example-1-2-30 | 4-MeBn- | i-Pr- |
| Example-1-2-31 | 4-Cyano-Bn- | —CH₂CH₂CO₂H |
| Example-1-2-32 | 4-Cyano-Bn- | —(CH₂)₃CO₂H |
| Example-1-2-33 | 4-MeO₂C-Bn- | 4-Py- |
| Example-1-2-34 | Ph- | i-Pr- |
| Example-1-2-35 | Ph- | 4-Py- |
| Example-1-2-36 | MeOCH₂CH₂— | i-Pr- |
| Example-1-2-37 | 4-HO(O)C-Bn- | 3,5-Dichloro-Ph- |
| Example-1-2-38 | 4-HO(O)C-Bn- | 4-Bromo-Ph- |
| Example-1-2-39 | 2-Py-CH₂— | 3,5-Dichloro-Ph- |
| Example-1-2-40 | 2-Py-CH₂— | 4-Bromo-Ph- |
| Example-1-2-41 | 4-Cyano-Bn- | —CH(Ph)CH₂CH₂COOH |
| Example-1-2-42 | 4-Cyano-Bn- | —CH₂CH₂CH(Ph)COOH |
| Example-1-2-43 | 4-Cyano-Bn- | —CH₂C(CH₃)₂CH₂CO₂H |
| Example-1-2-44 | 4-Cyano-Bn- | —CH₂CH(Ph)CO₂H |

Example 1-3-1

Preparation of N-butyl-N'-ethyl-N-{5-[2,2,2-trifluoro-1-hydroxy-1-(trifluoromethyl)ethyl]-1,3-thiazol-2-yl}urea

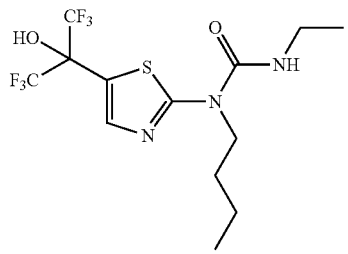

Step 1

Preparation of 2-[2-(butylamino)-1,3-thiazol-5-yl]-1,1,1,3,3,3-hexafluoropropan-2-ol 2-aminothiazole (1 g, 10 mmol) and butyraldehyde (1.44 g, 20 mmol) were mixed in dichloroethane (45 ml) and then treated with sodium triacetoxyborohydride (6 g, 28 mmol) and acetic acid (3.6 g 60 mmol). The reaction mixture was stirred at r.t. under a nitrogen atmosphere overnight. The reaction mixture then was quenched by 1N NaOH and extracted with EtOAc. The organic layer was washed with saturated NaHCO₃, brine and dried over MgSO₄. The solvent was evaporated to give 2-butylaminothiazole as a brown residue (1.02 g).

A catalytic amount of molecular sieves powder (4A) was added to the mixture of 2-butylaminothiazole (1 g 6.41 mmol) prepared above and hexafluoroacetone trihydrate (2.86 g 13 mmol). The mixture was heated to gently reflux at 100° C. overnight. EtOAc is added and the mixture was filtered. Solvent was evaporated under reduced pressure. The residue was recrystallized in THF and hexanes to afford the title compound as a white solid. (1.68 g). ¹H NMR δ0.95 (t, 3H), 1.40 (m, 2H), 1.6 (m, 2H), 3.20 (t, 2H), 7.3 (s, 1H); ESIMS: m/z 323 (M+H).

Step 2

To a mixture of 2-[2-(butylamino)-1,3-thiazol-5-yl]-1,1,1,3,3,3-hexafluoropropan-2-ol (65 mg, 0.202 mmol) obtained from step 1 in benzene (2 ml) was added ethyl isocyanate (24 μL, 0.3 mmol) under a nitrogen atmosphere The reaction mixture was refluxed for 4 h. Solvent was removed under reduced pressure to obtain an oil, which was dissolved in EtOAc. The resulting solution was washed with H₂O, saturated NaHCO₃ and brine, and dried over MgSO₄. The solvent was evaporated to yield a crude product which was purified by preparative TLC (EtOAC:hexanes, 1:3) to afford the corresponding product as a white solid (31 mg). ¹H NMR δ0.92 (t, 3H), 1.20 (t, 3H), 1.37 (m, 2H) 1.67 (m, 2H), 3.37 (q, 2H), 3.83 (t, 2H), 4.24 (brs, 1H), 7.50 (s, 1H), 8.60 (brs, 1H); ESIMS: m/z 392 (M−H).

TABLE 4

The following compounds are prepared in accordance with the procedure described in the above example 1-3-1.

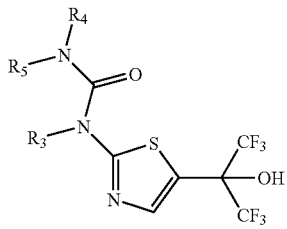

| Example | R₃ | R₄ | R₅ |
| --- | --- | --- | --- |
| Example 1-3-1 | n-Bu- | Et- | H |
| Example 1-3-2 | Et- | c-Hexyl- | H |
| Example 1-3-3 | 4-Cyano-Bn- | c-Hexyl- | H |
| Example 1-3-4 | 4-Cyano-Bn- | n-Pr- | H |
| Example 1-3-5 | 4-Cyano-Bn- | i-Pr- | H |
| Example 1-3-6 | 4-Cyano-Bn- | EtOC(O)CH₂— | H |
| Example 1-3-7 | n-Bu- | c-Hexyl- | H |
| Example 1-3-8 | Et- | Et- | H |
| Example 1-3-9 | 4-Py-CH₂— | Et- | H |

Example 1-4

Preparation of pyridin-4-yl methyl {5-[2,2,2-trifluoro-1-hydroxy-1-(trifluoromethyl)ethyl]-1,3-thiazol-2-yl}formamide

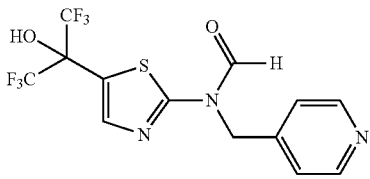

To acetic-formic anhydride (1.5 ml) was added 1,1,3,3,3-hexafluoro-2-{2-[(pyridin-4-1ylmethyl)amino]-1,3-thiazol-5-yl}propan-2-ol (72 mg, 0.201 mmol) obtained from step 1 of example 1-2-1. The reaction mixture was stirred at r.t. overnight and then concentrated under reduced pressure. The residue was dissolved in EtOAc and washed with H₂O, saturated NaHCO₃ and brine, then dried over MgSO₄. Solvent was evaporated to give a residue which was purified by preparative TLC(CHCl₃:CH₃OH, 95:5) to afford the title compound as a white solid (38 mg). (DMSO-d6) δ5.28 (s, 2H), 7.26 (d, 2H), 7.65 (s, 1H); 8.48 (d, 2H) 8.98 (s, 1H); 9.31 (brs, 1H); ESIMS: m/z 384 (M−H)

Example 2

Preparation of diethyl 5-[2,2,2-trifluoro-1-hydroxy-1-(trifluoromethyl)ethyl]-1,3-thiazol-2-yl-amidophosphate

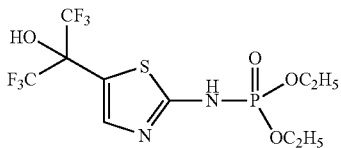

To a solution of (2-amino-1,3-thiazol-5-yl)-1,1,1,3,3,3-hexafluoropropan-2-ol (133 mg 0.5 mmol) from step 1 of example 1-1-1, DMAP (61 mg, 0.5 mmol), Et₃N (100 μL, 0.72 mmol) and CH₂Cl₂ (5 ml) was added diethyl chlorophosphate (87 μL, 06 mmol). The reaction mixture was stirred at r.t. for 96 h. Solvent was removed and EtOAc was added. The solution was washed with water. After removal of solvent, the residue was purified by a short Ion Exchange Column (Dowex-50W, ethanol) to afford the title compound as a white solid (43 mg). ¹H NMR (DMSO-d₆) δ 1.20 (t, 6H), 3.89 (m, 4H), 7.46 (s, 1H), 9.18 (s, 1 H); ESIMS: m/z 401 (M−H).

Example 3

Preparation of 4-chloro-N-{5-[2,2,2,-trifluoro-1-hydroxy-1-(trifluoromethyl)ethyl]-1,3-thiazol-2-yl}benzenesulfonamide

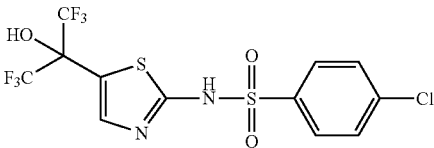

To a solution of (2-amino-1,3-thiazol-5-yl)-1,1,1,3,3,3-hexafluoropropan-2-ol (79.8 mg 0.3 mmol) from step 1 of example 1-1-1 in pyridine (1 ml) was added 4-chlorobenzensulfonyl chloride 63.3 mg (0.3 mmol). The reaction mixture was stirred at r.t. for 24 h. Pyridine was removed under reduced pressure to yield the residue, which was washed with 1N HCl to give a light brown solid. The solid was washed by water, saturated NaHCO₃, brine, and dried by vacuum. Further purification by preparative TLC(CHCl₃:CH₃OH, 90:10) afforded the title compound as a white solid (38.2 mg). ¹H NMR (DMSO-d6) δ7.55 (s, 1H), 7.60 (d, 2H), 7.78 (d, 2H), 9.50 (s, 1H), 13.2 (brs, 1H); ESIMS: m/z 439 (M−H).

Example 4

Preparation of N-ethyl-2-methyl-N-{5-[2,2,2-trifluoro-1-hydroxy-1-(trifluoromethyl)ethyl]-1,2,4-thiadiazol-3-yl}propanamide

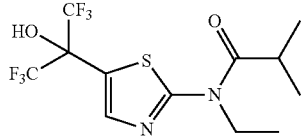

Step 1

To a solution of 2-(ethylamino)-1,3,4-thioadiazole (1.29 g, 10 mmol) in pyridine (5 ml) was added isobutyryl chloride (1.06 g, 10 mmol) at 0° C. The reaction mixture was stirred at r.t. overnight. Solvent was removed under reduced pressure and ethyl acetate was added. The organic layer was washed with $H_2O$ and brine and dried over $MgSO_4$. The solvent was evaporated and the residue was recrystallized in $CHCl_3$ and hexanes to afford the intermediate as an orange solid (1.05 g).

Step 2

To a solution of the intermediate (400 mg 2.0 mmol) prepared above in THF (12 ml) at −78° C., was added n-butyllithium in hexanes solution (2.5 M, 1.2 ml, 3.0 mmol) under a nitrogen atmosphere and the resulting solution was stirred at −78° C. for 30 minutes. Hexafluoroacetone (890 mg, 5.36 mmol) was bubbled into this solution and the resulting mixture was stirred at −78° C. for another 30 minutes. The reaction mixture was quenched with $H_2O$ and allowed to warm up. The solvent was removed and ethyl acetate was added. The organic layer was washed with aqueous $NH_4Cl$, $H_2O$, and brine, then dried ($MgSO_4$) and evaporated. Purification by preparative TLC (hexanes:ethyl acetate, 50:50) afforded the title compound as a white solid (186 mg). $^1H$ NMR ($DMSO_4$-d6) δ1.10 (d, 6H), 1.28 (t, 3H), 3.1 (m, 1H), 4.25 (q, 2H), 9.90 (brs, 1H); ESIMS: m/z 364 (M−H).

Example 5

Preparation of 1-{5-[2,2,2-trifluoro-1-hydroxy-1-(trifluoromethyl)ethyl]furan-2-yl}pentan-1-one

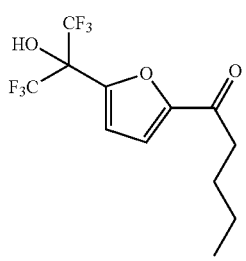

To a solution of 5-bromo-2-furoic acid (191 mg 1 mmol) in THF (8 ml), was added n-butyllithium in hexanes solution (2.5 M, 1.2 ml, 3 mmol) at −78° C. under a nitrogen atmosphere. The resulting mixture was stirred at −78° C. for 30 minutes. Hexafluoroacetone (1.2 g, 7.3 mmol) was bubbled into the reaction mixture and the resulting solution was stirred for another 30 minutes at −78° C. The reaction mixture was allowed to warm to r.t. and then quenched with $H_2O$. Solvent was evaporated, and the residue was dissolved in EtOAc. The organic layer was washed with $H_2O$ and brine, dried ($MgSO_4$) and evaporated. The residue was purified by preparative TLC (hexanes:ethyl acetate, 2:1) to afford the title compound (109 mg) as a yellow oil. $^1H$ NMR δ0.93 (t, 3H), 1.38 (m, 2H), 1.68 (m, 2H), 2.80 (t, 2H), 7.19 (d, 1H), 7.80 (d, 1H); ESIMS: m/z 319 (M+H).

Example 6

Preparation of 1,1-dimethylethyl 5-[2,2,2-trifluoro-1-hydroxy-1-(trifluoromethyl)ethyl]pyrimidin-2-yl-carbamate

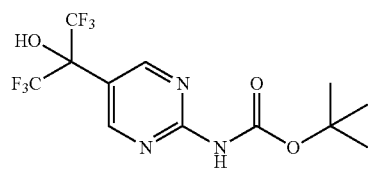

Step 1

To a mixture of 2-amino-5-bromopyridine (3.48 g 20 mmol), triethylamine 6.1 ml (43.7 mmol) and 4-(dimethylamino)-pyridine (244 mg 2 mmol) in THF (60 ml) was added di-t-butyl dicarbonate (9.82 g, 45 mmol). The reaction mixture was stirred at room temperature for 3 days. The solvent was removed under reduced pressure, and the residue was recrystallized in THF and hexanes. Further purification by flash-chromatography (silica gel, ethyl acetate:hexanes, 1:4) afforded di(t-butyl) 5-bromopyrimidodicarbonate (6.1 g) as a white solid.

Step 2

To a solution of intermediate described above (190 mg, 0.51 mmol) in THF (8 ml) at −100° C., was added n-butyllithium in hexanes solution (2.5 M, 0.8 ml, 2 mmol) under a nitrogen atmosphere, and the resulting reaction mixture was stirred at −100° C. for 30 minutes. Hexafluoroacetone (540 mg, 3.35 mmol) was bubbled into this mixture and the resulting solution was stirred at −100° C. for another 30 minutes. The reaction mixture was quenched with $H_2O$ and allowed to warm to r.t. Solvent was removed and ethyl acetate was added. The organic layer was washed with $H_2O$ and brine, dried ($MgSO_4$) and evaporated. Purification by preparative TLC (hexanes:ethyl acetate, 3:1) afforded the corresponding compound as a white solid (18.6 mg). $^1H$ NMR ($DMSO_4$-d6) δ1.40 (s, 9H), 8.86 (s, 2H), 9.2 (brs, 1H), 10.40 (brs, 1H); ESIMS: m/z 360 (M−H).

Example 7-1

Preparation of N-methyl-3-phenyl-N-[5,5,5-trifluoro-4-hydroxy-4-(trifluoromethyl) pent-2-ynyl] propanamide

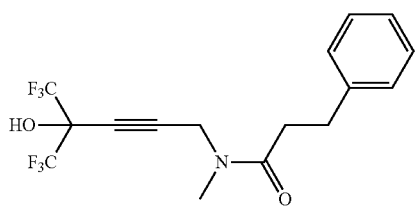

Step 1

To a solution of N-methylpropargylamine (691 mg, 10 mmol) and triethylamine (1.21 g, 12 mmol) in CH$_2$Cl$_2$ (40 ml) was added dropwise a solution of hydrocinnamoyl chloride (1.68 g 10 mmol) in CH$_2$Cl$_2$ (10 ml) at r.t. The reaction mixture was stirred at r.t. for 2 h. Solvent was removed under reduced pressure and the residue was dissolved in EtOAc. The organic layer was washed with water, brine and dried over MgSO$_4$. Concentration afforded the intermediate (1.72 g) as a brown oil, which was further dried by vacuum for several days.

Step 2

To a solution of intermediate prepared above (402 mg, 2 mmol) in ether (8 ml) at −78° C., was added n-butyllithium in hexanes solution (2.5 M, 1.2 ml, 3 mmol) under a nitrogen atmosphere. The resulting mixture was stirred at −78° C. for 90 minutes. Hexafluoroacetone (780 mg, 4.7 mmol) was bubbled into the reaction mixture and the resulting solution was stirred for another 30 minutes at −78° C. The reaction mixture was allowed to warm to r.t. and quenched with H$_2$O. The mixture was partitioned between ether and water. The organic layer was washed with H$_2$O and brine, dried (MgSO$_4$) and evaporated. The residue was recrystallized in ether and hexanes to afford the title compound (123 mg) as a white solid. $^1$H NMR δ2.62 (t, 2H), 2.92 (t, 2H), 2.95 (s, 3H), 4.26 (s, 2H), 7.02-7.30 (m, 5H) ESIMS: m/z 366 (M−H).

TABLE 5

The following compounds are prepared in accordance with the procedure described in the example 7-1.

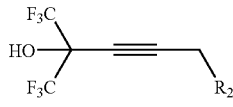

| Example 7 | R$_2$ |
|---|---|
| Example 7-1 | PhCH$_2$CH$_2$C(O)N(CH$_2$)— |
| Example 7-2 | PhCH$_2$N(CH$_2$)— |
| Example 7-3 | PhCH$_2$CH$_2$C(O)NH— |
| Example 7-4 | Ph- |
| Example 7-5 | PhS— |
| Example 7-6 | (n-Bu)$_2$N— |

Example 8-1

Preparation of ethyl 5-[2,2,2-trifluoro-1-hydroxy-1-(trifluoromethyl)ethyl]-4,5-dihydroisoxazole-3-carboxylate

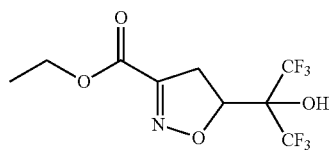

Step 1

Preparation of 1,1,1-trifluoro-2-trifluoromethyl-but-3-en-2-ol

To 1.6 M vinylmagnesium chloride in THF (200 mL, 0.32 mol) at −78° C. was added hexafluoroacetone (50 g, 0.31 mol) by cannula over a period of 3 h with stirring. The reaction mixture was allowed to warm to r.t. and stirred for an additional 2 h, then heated to 40° C. for an additional 1 h. The reaction mixture was quenched with aqueous NH$_4$Cl solution. The mixture was diluted with pentane, filtered, and the organic phase was dried over MgSO$_4$. Fractional distillation (12 inch Vigreux column) at 100-103° C. afforded the product 1,1,1-trifluoro-2-trifluoromethyl-but-3-en-2-ol (mixture containing around 66 mol % THF) as a clear liquid (50 g). $^1$H NMR δ 5.20 (br, 1H), 5.70 (d, 1H), 5.92 (m, 2H).

Step 2

Preparation of ethyl 5-[2,2,2-trifluoro-1-hydroxy-1-(trifluoromethyl)ethyl]-4,5-dihydroisoxazole-3-carboxylate To a solution of commercially available ethyl chlorooximidoacetate (3.03 g, 20 mmol) in 1,1,1-trifluoro-2-trifluoromethyl-but-3-en-2-ol (around 90 mmol) from step 1, was added a solution of triethylamine (2.23 g, 22 mmol) in THF (10 mL) by syringe pump over 68 h with stirring at r.t. The reaction mixture was filtered, and the filter cake was washed with ether and pentane. The filtrate was washed with dilute acid and water. Solvents were removed at atmospheric pressure and the residue was purified by column chromatography (EtOAc: Hexanes, 2:1) to afford the ethyl ester (3.06 g, 50%) as a white solid. $^1$H NMR δ 1.38 (t, 3H), 3.40 (dd, 1H), 3.60 (dd, 1H), 4.34 (q, 2H), 5.16 (t, 1H).

Example 8-2

Preparation of 5-[2,2,2-trifluoro-1-hydroxy-1-(trifluoromethyl)ethyl]-4,5-dihydroisoxazole-3-carboxylic acid

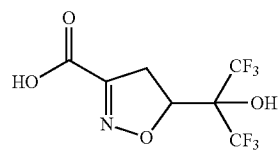

To a solution of ethyl 5-[2,2,2-trifluoro-1-hydroxy-1-(trifluoromethyl)ethyl]-4,5-dihydroisoxazole-3-carboxylate from example 8-1 (2.58 g, 8.34 mmol) in ethanol (5 ml) was added 1 N NaOH (16.7 mL). The mixture was stirred at r.t. for 1 h. Ethanol was removed under reduced pressure, and to the aqueous solution was added concentrated HCl (1.5 mL). The product was extracted 3 times with EtOAc and 2 times with isopropyl ether, and the combined organic layers were dried over MgSO$_4$. Solvents were removed under reduced pressure to afford the carboxylic acid intermediate as an off-white solid (2.30 g, 98%). $^1$H NMR (DMSO-d6) δ 3.2-3.4 (m, 2H), 5.12 (t, 3H), 8.6 (br, 1H); ESIMS: m/z 280 (M−H).

Example 8-3-1

Preparation of N-(1-Methyl hexyl)-5-[2,2,2-trifluoro-1-hydroxy-1-(trifluoromethyl)ethyl]-4,5-dihydroisoxazole-3-carboxamide

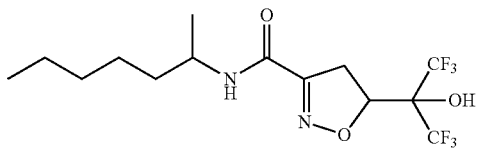

A solution of 5-[2,2,2-Trifluoro-1-hydroxy-1-(trifluoromethyl)ethyl]-4,5-dihydroisoxazole-3-carboxylic acid from example 8-2 (84 mg, 0.3 mmol), 2-aminoheptane (69 mg, 0.6 mmol), 4-methylmorpholine (121 mg, 1.2 mmol), and (benzotriazol-1-yloxy)tris(dimethylamino)phosphonium hexafluorophosphate (BOP) (265 mg, 0.6 mmol) in DMF (0.5 ml) was stirred at r.t. for 17 h. The reaction mixture was diluted with EtOAc, washed with water, 1 M citric acid and brine, then dried over $MgSO_4$. The solvent was removed under reduced pressure and the residue was purified by preparative TLC (EtOAc:Haxanes, 2:1) to afford the title compound as a clear oil (74 mg, 65%). $^1H$ NMR δ 0.86 (t, 3H), 1.16 (d, 3H), 1.27-1.45 (m, 8H), 3.39 (dd, 1H), 3.65 (dd, 1H), 3.99 (m, 1H), 5.11 (t, 1H), 6.36 (d, 1H). ESIMS: m/z 377 (M−H).

TABLE 6

The following compounds are prepared in accordance with the procedure described in the example 8-3.

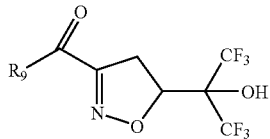

| Example | R$_9$ |
|---|---|
| Example 8-3-1 | 1-Methyl-hexyl-NH— |
| Example 8-3-2 | Pyrind-4yl-methyl-N(Et)- |
| Example 8-3-3 | (i-Pr)$_2$N— |
| Example 8-3-4 | (i-Bu)$_2$N— |
| Example 8-3-5 | PhCH$_2$CH$_2$N(Me)- |
| Example 8-3-6 | t-BuOC(O)CH$_2$CH$_2$NH— |
| Example 8-3-7 | BnNH— |
| Example 8-3-8 | (2-Pyridin-2-yl-ethyl)-N(Me)- |
| Example 8-3-9 | HOCH$_2$CH$_2$N(Et)- |
| Example 8-3-10 | Et(Ph)N(Me)- |
| Example 8-3-11 | EtOC(O)CH$_2$N(Bn)- |
| Example 8-3-12 | HO(O)CCH$_2$CH$_2$NH— |
| Example 8-3-13 | EtOC(O)CH$_2$CH$_2$NH— |
| Example 8-3-14 | 1-(2-Et-Piperidinyl)- |
| Example 8-3-15 | 1-(2-Me-Pyrrolidinyl)- |
| Example 8-3-16 | bis-(2-Ethyl-hexyl)N— |
| Example 8-3-17 | t-BuOC(O)CH(i-Pr)NH— |
| Example 8-3-18 | MeOC(O)CH$_2$CH$_2$COCH$_2$NH— |
| Example 8-3-19 | t-BuOCOCH(Bn)NH— |
| Example 8-3-20 | 1-Azepanyl- |
| Example 8-3-21 | 1-Piperidinyl- |
| Example 8-3-22 | 1-(2-Methyl-aziridinyl)- |
| Example 8-3-23 | (5-t-Butoxycarbonyl-2,5-diaza-bicyclo[2.2.1]hept-2-yl)- |
| Example 8-3-24 | (Isoamyl)$_2$N— |
| Example 8-3-25 | t-BuOC(O)CH$_2$CH$_2$N(i-Bu)- |
| Example 8-3-26 | EtOC(O)CH$_2$NH— |
| Example 8-3-27 | EtOC(O)(CH$_2$)$_3$NH— |
| Example 8-3-28 | 1-Azetidinyl- |
| Example 8-3-29 | 1-Pyrrolidinyl- |
| Example 8-3-30 | 1-(2,5-Dimethyl-pyrrolidinyl)- |
| Example 8-3-3 | (2-Oxa-5-aza-bicyclo[2.2.1]hept-5-yl)- |
| Example 8-3-32 | i-BuNH— |
| Example 8-3-33 | c-PrCH$_2$N(n-Pr)- |
| Example 8-3-34 | 2-Ethyl-hexyl-N(pyridin-2-ylmethyl)N— |
| Example 8-3-35 | t-BuCH$_2$CH$_2$NH— |
| Example 8-3-36 | EtOC(O)CH$_2$CH(CO$_2$Et)NH— |
| Example 8-3-37 | EtOC(O)CH(i-Bu)NH— |
| Example 8-3-38 | t-BuOCO(CH$_2$)$_2$CH(CO$_2$Me)NH— |
| Example 8-3-39 | 1-(2-CO$_2$Me)-Piperidinyl- |
| Example 8-3-40 | Pyridin-2-ylmethyl-NH— |
| Example 8-3-41 | Pyridin-3-ylmethyl-NH— |
| Example 8-3-42 | Pyridin-4-ylmethyl-NH— |
| Example 8-3-43 | Pyridin-2-yl-NH— |
| Example 8-3-44 | Pyridin-3-yl-methyl-N(Me)- |
| Example 8-3-45 | (EtO)$_2$C(O)CH(Me)NH— |
| Example 8-3-46 | i-BuN(Me)- |
| Example 8-3-47 | t-BuOC(O)CH(s-Bu)NH— |

Example 9-1

Preparation of 2-(3-bromo-4,5-dihydroisoxazol-5-yl)-1,1,1,3,3,3-hexafluoropropan-2-ol

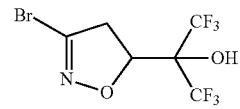

To a solution of glyoxylic acid (1.11 g 15 mmol) in 1.2 ml of $H_2O$ was added a solution of hydroxylamine (0.5 g 15 mmol) in 1 ml of water. The solution was stirred at r.t. for 18 h, then mixed with 10 ml ethylene glycol dimethyl ether. To the stirring solution was added NBS (5.16 g, 29 mmol) over 0.5 h at 0° C. The reaction mixture was allowed to warm to r.t. and stirred for another 0.5 hr. The organic layer was separated and water layer was extracted with ether. The combined and concentrated organic layers (around 10 ml) were added dropwise by syringe pump at r.t. over 4 days to a stirred mixture composed of 1,1,1-trifluoro-2-trifluoromethyl-but-3-en-2-ol (30 mmol, from example 8-1, step 1), potassium bicarbonate (6 g, 60 mmol) and 1 ml water. The reaction mixture was neutralized with 5 N HCl and partitioned between ether and water. The organic layer was separated and washed with brine, dried over $MgSO_4$, and evaporated to dryness. A white solid in 13% yield was obtained by Kugelrohr distillation (oven temperature, 80-100° C./15-30 m_r). ¹H NMR (DMSO-d6) δ3.40 (dd, 1H), 3.50 (dd, 1H), 5.20 (t, 1H), 8.70 (s, 1H) ESIMS: m/z 315 (M–H).

Example 9-2

Preparation of 1,1,1,3,3,3-hexafluoro-2-(3-pyrrolidin-1-4,5-dihydroisoxazol-5-yl)propan-2-ol

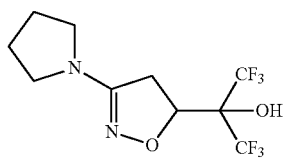

A mixture of 2-(3-bromo-4,5-dihydroisoxazol-5-yl)-1,1,1,3,3,3-hexafluoropropan-2-ol (31.6 mg, 0.1 mmol) from example 9-1 and pyrrolidine (28.2 mg, 0.4 mmol) in dioxane (0.5 ml) was heated at 85° C. for 48 h. The mixture was concentrated under reduced pressure and diluted with EtOAc. The organic layer was washed with brine and dried over MgSO₄. Solvent was evaporated under reduced pressure, and the residue was recrystallized from CHCl₃ and hexanes to afford the title compound as a light brown solid (17.8 mg). ¹H NMR δ 1.94 (m, 4H), 3.10 (dd, 1H), 3.28 (m, 4H), 3.90 (dd, 1H), 4.0 (br, 1H), 4.86 (t, 3H); ESIMS: m/z 337 (M+H).

Example 10

Preparation of 3-isopropyl-1-pentyl)-1-[5-(2,2,2-trifluoro-1hydroxy-1-trifluoromethyl-ethyl)-4,5-dihydroisoxazol-3-yl]-urea

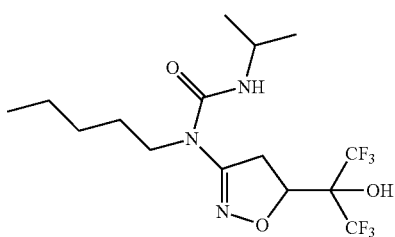

Step 1

A mixture of 2-(3-bromo-4,5-dihydroisoxazol-5-yl)-1,1,1,3,3,3-hexafluoropropan-2-ol from example 9-1 (31.6 mg g, 0.1 mmol) and amylamine (26.1 mg, 0.3 mmol) in 0.5 ml of triethylamine was heated at 110° C. in a pressure tube overnight. The reaction mixture was concentrated under vacuum for 5 h to dryness. The residue was directly used as a starting material for next step.

Step 2

To a mixture of the residue from step 1 in 0.5 ml of toluene was added isopropyl isocyanate (30 μL, 0.3 mmol). The reaction mixture was heated at 110° C. in a pressure tube overnight. The organic solvent was removed under reduced pressure and the residue was partitioned between EtOAc and water. The organic layer was washed with water and brine, dried (MgSO₄) and concentrated to dryness. The crude product was purified by preparative TLC (Silica gel, CHCl₃:CH₃OH, 10:1) to afford the title compound (22.2 mg) as an oil. ¹H NMR δ0.83 (t, 3H), 1.15 (d, 3H), 1.17 (d, 3H), 1.30 (m, 4H), 1.57 (m, 2H), 3.25 (d, d, 1H), 3.57 (m, 2H), 3.64 (d, d, 1H), 3.95 (m, 1H), 4.36 (br, 1H), 4.96 (t, 1H), 7.65 (d, 1H); ESIMS: m/z 408 (M+H).

Example 11-1

Preparation of 1,1,1,3,3,3-hexafluoro-2-[3-(4-methylphenyl)-4,5-dihydroisoxazol-5-yl]propan-2-ol

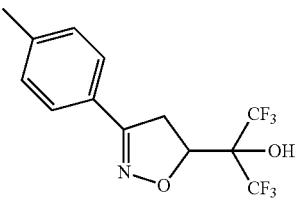

Step 1

To a mixture of p-tolualdehyde (1.2 g 10 mmol) and hydroxylamine hydrochloride (700 mg 10 mmol) in 30 ml ethanol was added sodium methoxide (540 mg, 10 mmol). The reaction mixture was stirred at r.t. for 8 h. The mixture was filtered and evaporated to dryness. The resulting white solid was diluted with 30 ml CH₂Cl₂, to which NCS (1.33 g, 10 mmol) was added. The reaction mixture was stirred at r.t overnight. The mixture was filtered. Solvent was removed and the residue was purified by flash chromatography on silica gel (hexane:ethyl acetate, 3:1) to give a solid in a 44% yield.

Step 2

To a stirred solution of the above compound (170 mg, 1 mmol) in 1,1,1-trifluoro-2-trifluoromethyl-but-3-en-2-ol (2 mmol) was added a solution of triethylamine (121 mg, 1.2 mmol) in THF (10 ml) dropwise by syringe pump at r.t. over 30 h. The mixture was concentrated under reduced pressure and diluted with EtOAc. The organic layer was washed with 1 N HCl, H₂O and dried over MgSO₄. Solvent was evaporated under reduced pressure, and the residue was purified by preparative TLC (Hexanes:EtOAc, 5:1) to afford the title compound as a white solid (89.2 mg).
¹H NMR δ 2.38 (s, 3H), 3.50 (d,d, 2H), 3.64 (br, 1H), 3.69 (dd, 2H), 5.08 (t, 1H), 7.20 (d, 2H), 7.60 (d, 2 H); ESIMS: m/z 342 (M–H).

TABLE 7

The following compounds are prepared in accordance with the procedure described in the example 11-1.

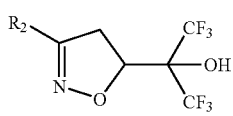

| Example | R₂ |
|---|---|
| Example 11-1 | p-Tolyl- |
| Example 11-2 | p-CN-Ph- |
| Example 11-3 | 5-Methylfuryl- |

TABLE 7-continued

| | |
|---|---|
| Example 11-4 | p-Bromo-Ph- |
| Example 11-5 | 5-(1-Me-2-Cl-pyrrolyl)- |

Example 12

Preparation of (4-Chloro-phenyl)-[5-(2,2,2-trifluoro-1-hydroxy-1-trifluoromethyl-ethyl)-4,5-dihydroisoxazol-3-yl]methanone

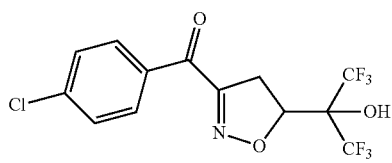

To a solution of commercially available 4-chlorophenyl glyoxylohydroxamyl chloride (218 mg, 1 mmol) in 1,1,1-trifluoro-2-trifluoromethyl-but-3-en-2-ol (2 mmol) was added a solution of triethylamine (111 mg, 1.1 mmol) in THF (10 ml) dropwise by syringe pump at r.t. over 30 h. The mixture was concentrated under reduced pressure and diluted with EtOAc. The organic layer was washed with 1N HCl, H$_2$O and dried over MgSO$_4$. Solvent was evaporated under reduced pressure and the residue was purified by preparative TLC (Hexanes:EtOAc, 4:1) to afford the title compound as a white solid (107.3 mg). $^1$H NMR δ 3.54 (s, 1H), 3.60 (dd, 1H), 3.76 (dd, 1H), 5.12 (t, 1H), 7.45 (d, 2H), 8.14 (d, 2 H); ESIMS: m/z 374 (M–H).

Example 13

Preparation of (4-Chloro-phenyl)-[5-(2,2,2-trifluoro-1-hydroxy-1-trifluoromethyl-ethyl)-isoxazol-3-yl]methanone

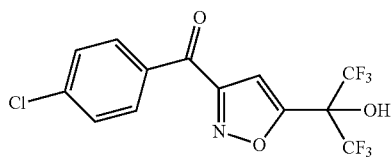

Step 1

Preparation of 1,1,1-trifluoro-2-trifluoromethyl-but-3-yn-2-ol

To a 100 ml solution of ethynyl magnesium bromide (0.5 M in THF) in an acetone-ethanol dry ice bath was bubbled hexafluoro acetone gas (6.1 g, 36.7 mmol) over 2 h. The reaction mixture was warmed to r.t and then refluxed for 0.5 h. The reaction mixture was quenched with aqueous NH$_4$Cl solution and extracted with ether. The combined organic phases were washed with brine, and dried over MgSO$_4$. A liquid mixture of 1,1,1-trifluoro-2-trifluoromethyl-but-3-yn-2-ol with THF at b.p. 100-103° C. (4.7 g, contained about 68 mol % THF) was obtained by distillation (12 inch Vigreux column).

Step 2

To a solution of commercially available 4-chlorophenyl glyoxylohydroxamyl chloride (109 mg, 0.5 mmol) in 1,1,1-trifluoro-2-trifluoromethyl-but-3-yn-2-ol from step 1 (about 1 mmol) was added a solution of triethylamine (60 mg, 0.6 mmol) in THF (10 ml) dropwise by syringe pump at r.t. over 30 h. The mixture was concentrated under reduced pressure and diluted with EtOAc. The organic layer was washed with 1N HCl, H$_2$O and dried over MgSO$_4$. Solvent was evaporated under reduced pressure and the residue was purified by preparative TLC (Hexanes:EtOAc, 5:1) to afford the title compound as a white solid (87.2 mg). $^1$H NMR (DMSO-d$_6$) δ 7.37 (s, 1H), 7.60 (d, 2 H), 8.14 (d, 2H), 9.92 (s, 1H); ESIMS: m/z 372 (M–H).

We claim:
1. A compound of the formula:

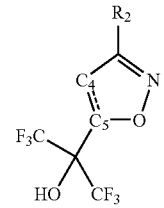

wherein:
the dashed line between C$_4$ and C$_5$ indicates that C$_4$ and C$_5$ are attached to each other by either a single bond or a double bond;
R$_2$ is selected from R$_9$C(═O)—, bromo, N-pyrrolidinyl, 3-isopropyl-2-pentyl-3-urea, p-tolyl, p-CN-Ph, 5-methylfuryl, p-bromo-Ph, and 5-(1-Me-2-Cl-pyrroly1); and
R$_9$ is selected from: 1-methyl-hexyl-NH—, pyrind-4ylmethyl-N(Et)-, (i-Bu)$_2$N—, PhCH$_2$CH$_2$N(Me)-, t-BuOC(O)CH$_2$CH$_2$NH—, BnNH, (2-pyridin-2-ylethyl)-N(Me)-, HOCH$_2$CH$_2$N(Et), Et(Ph)N(Me), EtOC(O)CH$_2$N(Bn), HO(O)CCH$_2$CH$_2$NH, EtOC(O)CH$_2$CH$_2$NH, 1-(2-Et-piperidinyl), 1-(2-Me-pyrrolidinyl), bis-(2-ethyl-hexyl)N, t-BuOC(O)CH(i-Pr)NH, MeOC(O)CH$_2$CH$_2$COCH$_2$NH, t-BuOCOCH(Bn)NH, 1-Azepanyl, 1-piperidinyl, 1-(2-methylaziridinyl), (5-t-butoxycarbonyl-2,5-diaza- bicyclo[2.2.1]hept-2-yl), (isoamyl)$_2$N, t-BuOC(O)CH$_2$CH$_2$N(i-Bu), EtOC(O)CH$_2$NH, EtOC(O)(CH$_2$)$_3$NH, 1-azetidinyl, 1-pyrrolidinyl, 1-(2,5-dimethylpyrrolidinyl), (2-Oxa-5-aza-bicyclo[2.2.1]hept-5-yl), i-BuNH, c-PrCH$_2$N(n-Pr), 2-ethyl-hexyl-N(pyridin-2-ylmethyl) N, t-BuCH$_2$CH$_2$NH, EtOC(O)CH$_2$CH(CO$_2$Et)NH, EtOC(O)CH(i-Bu)NH, t-BuOCO(CH$_2$)$_2$ CH(CO$_2$,Me)NH, 1-(2CO$_2$Me)-piperidinyl, pyridin-2-ylmethyl-NH, pyridin-3-ylmethyl-NH, pyridin-4-ylmethyl-NH, pyridin-2-yl-NH, pyridin-3-yl-methyl- N(Me), (EtO)$_2$C(O)CH(Me)NH, i-BuN(Me), t-BuOC(O)CH(s-Bu)NH—, ethoxy, hydroxyl, and 4-chloro-phenyl-;
or a pharmaceutically acceptable salt thereof.

2. A compound selected from the group consisting of:

N,N-bis(2-Methylpropyl)-5-[2,2,2-trifluoro-1-hydroxy-1-(trifluoromethyl)ethyl]-4,5-dihydroisoxazole-3-carboxamide;

1,1-Dimethylethyl 3-[({5-[2,2,2-trifluoro-1-hydroxy-1-(trifluoromethyl)ethyl]-4,5-dihydroisoxazol-3-yl}carbonyl)amino]propanoate;

1,1-Dimethylethyl 3-methyl-2-[({5-[2,2,2-trifluoro-1-hydroxy-1-(trifluoromethyl)ethyl]-4,5-dihydroisoxazol-3-yl}carbonyl)amino]butanoate;

N-(2-Ethylhexyl)-N-(pyridin-2-ylmethyl)-5-[2,2,2-trifluoro-1-hydroxy-1-(trifluoromethyl)ethyl]-4,5-dihydroisoxazole-3-carboxamide;

N-(1-Methylhexyl)-5[2,2,2-trifluoro-1-hydroxy-1-(trifluoromethyl)ethyl]-4,5-dihydroisoxazole-3-carboxamide;

N-(Pyridin-3-ylmethyl)-5-[2,2,2-trifluoro-1-hydroxy-1-(trifluoromethyl)ethyl]-4,5-dihydroisoxazole-3-carboxamide;

N-[(6,6-Dimethylbicyclo[3.1.1]hept-2-yl)methyl]-5[2,2,2-trifluoro-1-hydroxy-1-(trifluoromethyl)ethyl]-4,5-dihydroisoxazole-3-carboxamide;

3-(Methyl)-2-{[5-(2,2,2-trifluoro-1-hydroxy-1-(trifluoromethyl)ethyl)-4,5-dihydroisoxazole-3-carbonyl]-amino}-pentanoic acid tert-butyl ester;

4-{5-[2,2,2-Trifluoro-1-hydroxy-1-(trifluoromethyl)ethyl]-4,5-dihydroisoxazol-3-Yl}benzonitrile;

4-Chloro-phenyl)-[5-(2,2,2-trifluoro-1-hydroxy-1-trifluoromethyl-ethyl)-isoxazol-3-yl]methanone;

1,1,1,3,3,3-Hexafluoro-2-(3-pyrrolidin-1-4,5-dihydroisoxazol-5-yl)propan-2-ol;

3-(Isopropyl-1-pentyl)-1-[5(2,2,2-trifluoro-1hydroxy-1-trifluoromethyl-ethyl)-4,5-dihydroisoxazol-3-yl]-urea; and (4-chloro-phenyl)-[5-(2,2,2-trifluoro-1-hydroxy-1-trifluormethyl-ethyl)-4,5-dihydroisoxazol-3-yl]methanone;

or a pharmaceutically acceptable salt thereof.

3. A pharmaceutical composition comprising a compound of claim 1, or a pharmaceutically acceptable salt thereof, in association with a pharmaceutically acceptable carrier.

4. A pharmaceutical composition comprising a compound of claim 2, or a pharmaceutically acceptable salt thereof, in association with a pharmaceutically acceptable carrier.

* * * * *